(12) United States Patent
DeMers et al.

(10) Patent No.: US 12,367,632 B2
(45) Date of Patent: *Jul. 22, 2025

(54) METHOD AND DEVICE FOR SURFACING ACCUMULATED STRAIN INFORMATION

(71) Applicant: Apple Inc., Cupertino, CA (US)

(72) Inventors: Matthew S. DeMers, Lexington, KY (US); Adeeti V. Ullal, Los Altos, CA (US); Alexander G. Bruno, Cupertino, CA (US); Daniel M. Trietsch, San Jose, CA (US); Ioana Negoita, San Jose, CA (US); James J. Dunne, San Francisco, CA (US); Thomas G. Salter, Foster City, CA (US); Thomas J. Moore, Northglenn, CO (US)

(73) Assignee: APPLE INC., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/631,381

(22) Filed: Apr. 10, 2024

(65) Prior Publication Data
US 2024/0257430 A1 Aug. 1, 2024

Related U.S. Application Data

(63) Continuation of application No. 18/200,540, filed on May 22, 2023, now Pat. No. 12,002,140.
(Continued)

(51) Int. Cl.
*G09G 5/00* (2006.01)
*A61B 5/00* (2006.01)
(Continued)

(52) U.S. Cl.
CPC ............ *G06T 13/40* (2013.01); *A61B 5/744* (2013.01); *G06F 3/012* (2013.01); *G06T 11/206* (2013.01); *G06T 13/80* (2013.01); *G06T 2200/24* (2013.01)

(58) Field of Classification Search
CPC ....... A61B 5/1116; A61B 5/744; G06F 3/012; G06T 11/206; G06T 13/40; G06T 13/80; G06T 2200/24
See application file for complete search history.

(56) References Cited

U.S. PATENT DOCUMENTS

2021/0315458 A1 * 10/2021 Chahine ................. A61B 5/282

OTHER PUBLICATIONS

Rubo et al., "Visuo-tactile Congruency influences the Body Schema during Full Body Ownership Illusion", Consciousness and Cognition, Jan. 14, 2019, pp. 1-23.
(Continued)

*Primary Examiner* — Insa Sadio
(74) *Attorney, Agent, or Firm* — Fernando & Partners, LLP

(57) ABSTRACT

A method includes: presenting a posture summary interface including: a representation of the user, a visualization of a current accumulated strain value for the user, and a first affordance for initiating an animated posture summary associated with the accumulated strain value for the user over a respective time window; and in response to detecting a user input directed to the first affordance within the posture summary interface, presenting an animation of the representation of the user over the respective time window that corresponds to one or more instances in which head pose information changes associated with the user caused an increase or a decrease to the accumulated strain value greater than a significance threshold, wherein an appearance of the visualization of the current accumulated strain value for the user changes to represent the accumulated strain value for the user over the respective time window.

20 Claims, 16 Drawing Sheets

Related U.S. Application Data

(60) Provisional application No. 63/344,738, filed on May 23, 2022.

(51) Int. Cl.
    *G06F 3/01*           (2006.01)
    *G06T 11/20*         (2006.01)
    *G06T 13/40*         (2011.01)
    *G06T 13/80*         (2011.01)

(56) References Cited

OTHER PUBLICATIONS

Van Der Veen et al., "Effects of Avatar Perspective on Joint Excursions Used to Play Virtual Dodgeball: Within-Subject Comparative Study", JMIR Serious Games 2020, vol. 8, Iss. 3, pp. 1-14.

Sarig-Bahat et al., "Neck Pain Assessment in a Virtual Environment", Spine vol. 35, No. 4, pp. E105-E112.

Bergstrom et al., "First-Person Perspective Virtual Body Posture Influences Stress: A Virtual Reality Body Ownership Study", PLOS One, DOI: 10,1371/journal.pone.0148060, Feb. 1, 2016, pp. 1-21.

Roosink et al., "Real-time modulation of visual feedback on human full-body movements in a virtual mirror: development and proof-of-concept", Journal of NeuroEngineering and Rehabilitation 2015, 12:2, 10 pages.

Waltemate, "Creating a Virtual Mirror for Motor Learning in Virtual Reality", Bielefeld 2018, 131 pages.

\* cited by examiner

METHOD AND DEVICE FOR SURFACING ACCUMULATED STRAIN INFORMATION

CROSS-REFERENCE TO RELATED APPLICATIONS

This application is a continuation of U.S. patent application Ser. No. 18/200,540, filed on May 22, 2023, which claims priority to U.S. Provisional Patent App. No. 63/344,738, filed on May 23, 2022, which are both hereby incorporated by reference in their entirety.

TECHNICAL FIELD

The present disclosure generally relates to posture awareness and, in particular, to systems, devices, and methods for surfacing accumulated strain information.

BACKGROUND

Many persons may spend a significant number of hours at their computers or other devices during both work and non-work hours. This time spent using a computer or other devices may negatively impact the posture of said person.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1:
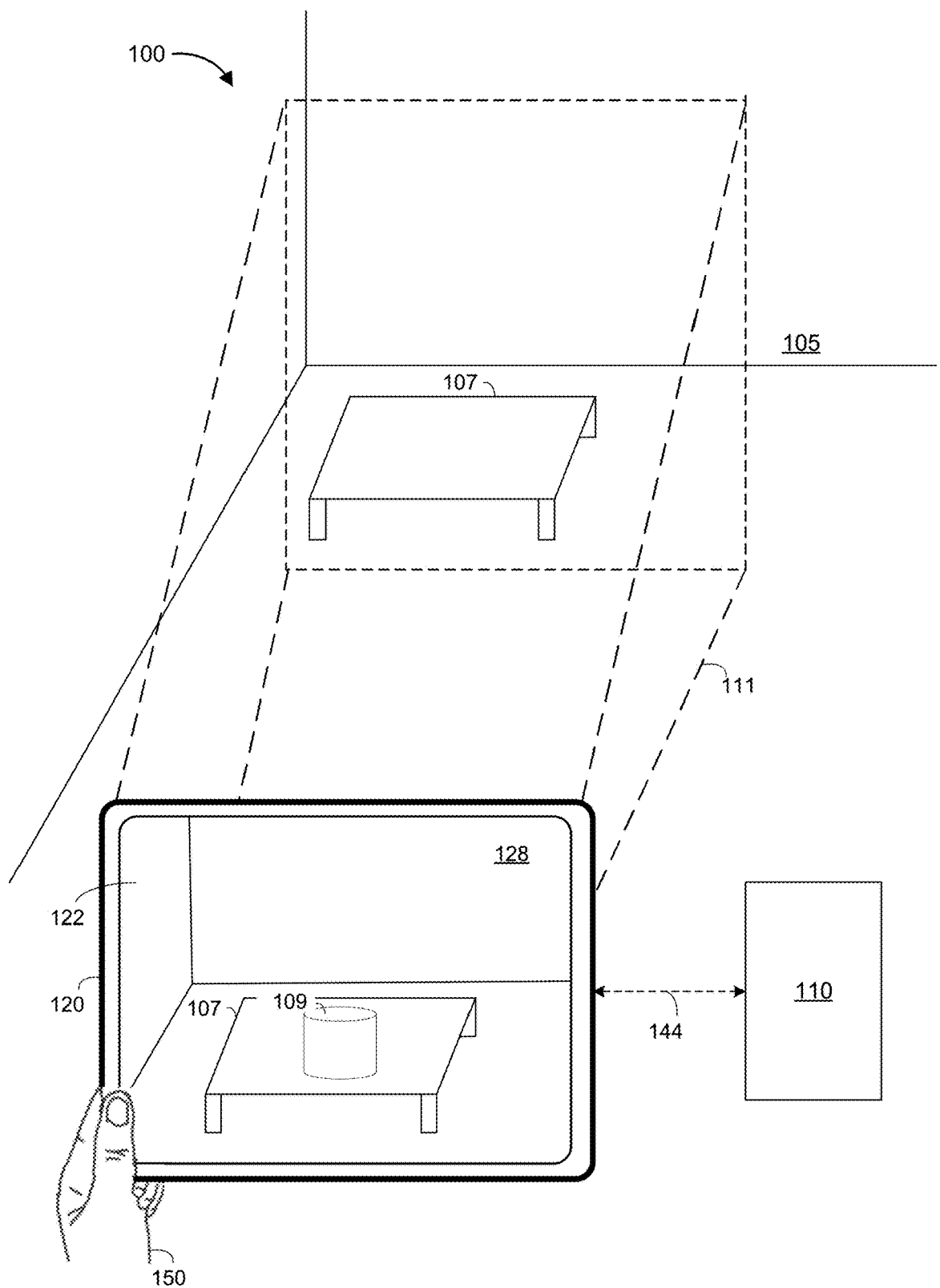
FIG. 1 is a block diagram of an example operating architecture in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

SUMMARY

Various implementations disclosed herein include devices, systems, and methods for surfacing accumulated strain information. According to some implementations, the method is performed at a computing system including non-transitory memory and one or more processors, wherein the computing system is communicatively coupled to a display device and one or more input devices. The method includes: presenting, via the display device, a posture summary interface including: a representation of the user, a visualization of a current accumulated strain value for the user, and a first affordance for initiating an animated posture summary associated with the accumulated strain value for the user over a respective time window; detecting a user input, via the one or more input devices, directed to the first affordance within the posture summary interface; and in response to detecting the user input directed to the first affordance within the posture summary interface, presenting, via the display device, an animation of the representation of the user over the respective time window that corresponds to one or more instances in which head pose information changes associated with the user caused an increase or a decrease to the accumulated strain value greater than a significance threshold, wherein an appearance of the visualization of the current accumulated strain value for the user changes to represent the accumulated strain value for the user over the respective time window.

In accordance with some implementations, an electronic device includes one or more displays, one or more processors, a non-transitory memory, and one or more programs; the one or more programs are stored in the non-transitory memory and configured to be executed by the one or more processors and the one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more displays, one or more processors, a non-transitory memory, and means for performing or causing performance of any of the methods described herein.

In accordance with some implementations, a computing system includes one or more processors, non-transitory memory, an interface for communicating with a display device and one or more input devices, and one or more programs; the one or more programs are stored in the non-transitory memory and configured to be executed by the one or more processors and the one or more programs include instructions for performing or causing performance of the operations of any of the methods described herein. In accordance with some implementations, a non-transitory computer readable storage medium has stored therein instructions which when executed by one or more processors of a computing system with an interface for communicating with a display device and one or more input devices, cause the computing system to perform or cause performance of the operations of any of the methods described herein. In accordance with some implementations, a computing system includes one or more processors, non-transitory memory, an interface for communicating with a display device and one or more input devices, and means for performing or causing performance of the operations of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

FIG. 1 is a block diagram of an example operating architecture 100 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating architecture 100 includes an optional controller 110 and an electronic device 120 (e.g., a tablet, mobile phone, laptop, near-eye system, wearable computing device, or the like).

In some implementations, the controller 110 is configured to manage and coordinate an extended reality (XR) experience (sometimes also referred to herein as a "XR environment" or a "virtual environment" or a "graphical environment") for a user 150 and optionally other users. In some implementations, the controller 110 includes a suitable combination of software, firmware, and/or hardware. The controller 110 is described in greater detail below with respect to FIG. 2. In some implementations, the controller 110 is a computing device that is local or remote relative to the physical environment 105. For example, the controller 110 is a local server located within the physical environment 105. In another example, the controller 110 is a remote server located outside of the physical environment 105 (e.g., a cloud server, central server, etc.). In some implementations, the controller 110 is communicatively coupled with the electronic device 120 via one or more wired or wireless communication channels 144 (e.g., BLUETOOTH, IEEE 802.11x, IEEE 802.16x, IEEE 802.3x, etc.). In some implementations, the functions of the controller 110 are provided by the electronic device 120. As such, in some implementations, the components of the controller 110 are integrated into the electronic device 120.

In some implementations, the electronic device 120 is configured to present audio and/or video (A/V) content to the user 150. In some implementations, the electronic device 120 is configured to present a user interface (UI) and/or an XR environment 128 to the user 150. In some implementations, the electronic device 120 includes a suitable combination of software, firmware, and/or hardware. The electronic device 120 is described in greater detail below with respect to FIG. 3.

According to some implementations, the electronic device 120 presents an XR experience to the user 150 while the user 150 is physically present within a physical environment 105 that includes a table 107 within the field-of-view (FOV) 111 of the electronic device 120. As such, in some implementations, the user 150 holds the electronic device 120 in his/her hand(s). In some implementations, while presenting the XR experience, the electronic device 120 is configured to present XR content (sometimes also referred to herein as "graphical content" or "virtual content"), including an XR cylinder 109, and to enable video pass-through of the physical environment 105 (e.g., including the table 107 or a representation thereof) on a display 122. For example, the XR environment 128, including the XR cylinder 109, is volumetric or three-dimensional (3D).

In one example, the XR cylinder 109 corresponds to head/display-locked content such that the XR cylinder 109 remains displayed at the same location on the display 122 as the FOV 111 changes due to translational and/or rotational movement of the electronic device 120. As another example, the XR cylinder 109 corresponds to world/object-locked content such that the XR cylinder 109 remains displayed at its origin location as the FOV 111 changes due to translational and/or rotational movement of the electronic device 120. As such, in this example, if the FOV 111 does not include the origin location, the displayed XR environment 128 will not include the XR cylinder 109. As another example, the XR cylinder 109 corresponds to body-locked content such that it remains at a positional and rotational offset from the body of the user 150. In some examples, the electronic device 120 corresponds to a near-eye system, mobile phone, tablet, laptop, wearable computing device, or the like.

In some implementations, the display 122 corresponds to an additive display that enables optical see-through of the physical environment 105 including the table 107. For example, the display 122 corresponds to a transparent lens, and the electronic device 120 corresponds to a pair of glasses worn by the user 150. As such, in some implementations, the electronic device 120 presents a user interface by projecting the XR content (e.g., the XR cylinder 109) onto the additive display, which is, in turn, overlaid on the physical environment 105 from the perspective of the user 150. In some implementations, the electronic device 120 presents the user interface by displaying the XR content (e.g., the XR cylinder 109) on the additive display, which is, in turn, overlaid on the physical environment 105 from the perspective of the user 150.

In some implementations, the user 150 wears the electronic device 120 such as a near-eye system. As such, the electronic device 120 includes one or more displays for displaying the XR content (e.g., a single display or one for each eye). For example, the electronic device 120 encloses the FOV of the user 150. In such implementations, the electronic device 120 presents the XR environment 128 by displaying data corresponding to the XR environment 128 on the one or more displays or by projecting data corresponding to the XR environment 128 onto the retinas of the user 150.

In some implementations, the electronic device 120 includes an integrated display (e.g., a built-in display) that displays the XR environment 128. In some implementations, the electronic device 120 includes a head-mountable enclosure. In various implementations, the head-mountable enclosure includes an attachment region to which another device with a display can be attached. For example, in some implementations, the electronic device 120 can be attached to the head-mountable enclosure. In various implementations, the head-mountable enclosure is shaped to form a receptacle for receiving another device that includes a display (e.g., the electronic device 120). For example, in some implementations, the electronic device 120 slides/snaps into or otherwise attaches to the head-mountable enclosure. In some implementations, the display of the device attached to the head-mountable enclosure presents (e.g., displays) the XR environment 128. In some implementations, the electronic device 120 is replaced with an XR chamber, enclosure, or room configured to present XR content in which the user 150 does not wear the electronic device 120.

In some implementations, the controller 110 and/or the electronic device 120 cause an XR representation of the user 150 to move within the XR environment 128 based on movement information (e.g., body pose data, eye tracking data, hand/limb/finger/extremity tracking data, etc.) from the electronic device 120 and/or optional remote input devices within the physical environment 105. In some implementations, the optional remote input devices correspond to fixed or movable sensory equipment within the physical environment 105 (e.g., image sensors, depth sensors, infrared (IR) sensors, event cameras, microphones, etc.). In some implementations, each of the remote input devices is configured to collect/capture input data and provide the input data to the controller 110 and/or the electronic device 120 while the user 150 is physically within the physical environment 105. In some implementations, the remote input devices include microphones, and the input data includes audio data associated with the user 150 (e.g., speech samples). In some implementations, the remote input devices include image sensors (e.g., cameras), and the input data includes images of the user 150. In some implementations, the input data characterizes body poses of the user 150 at different times. In some implementations, the input data characterizes head poses of the user 150 at different times. In some implementations, the input data characterizes hand tracking information associated with the hands of the user 150 at different times. In some implementations, the input data characterizes the velocity and/or acceleration of body parts of the user 150 such as his/her hands. In some implementations, the input data indicates joint positions and/or joint orientations of the user 150. In some implementations, the remote input devices include feedback devices such as speakers, lights, or the like.

Figure 2:
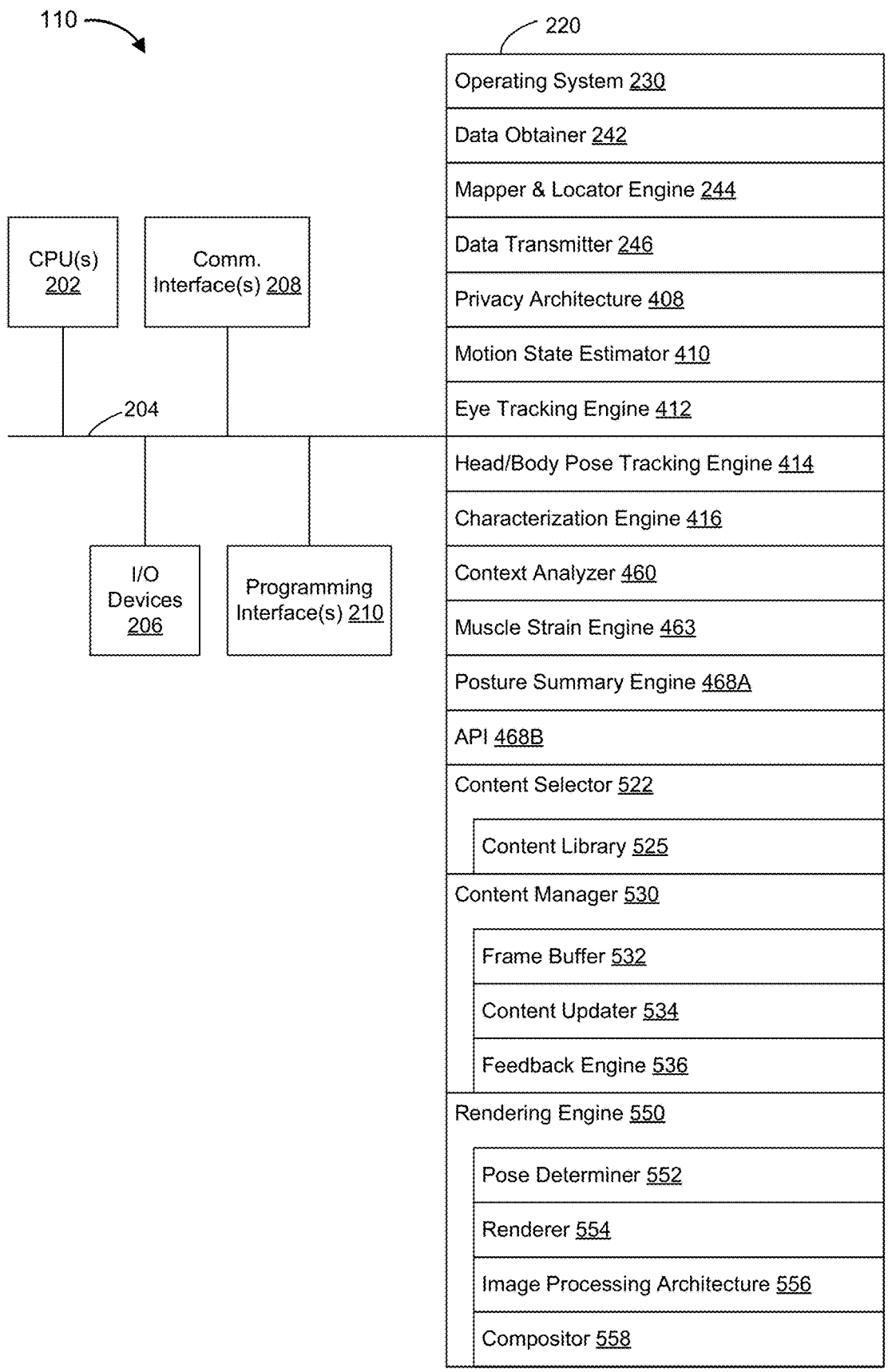
FIG. 2 is a block diagram of an example controller in accordance with some implementations.

FIG. 2 is a block diagram of an example of the controller 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some implementations, the one or more communication buses 204 include circuitry that interconnects and controls communications between system components. In some implementations, the one or more I/O devices 206 include at least one of a keyboard, a mouse, a touchpad, a touchscreen, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RAM), or other random-access solid-state memory devices. In some implementations, the memory 220 includes non-volatile memory such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some implementations, the memory 220 or the non-transitory computer readable storage medium of the memory 220 stores the following programs, modules and data structures, or a subset thereof described below with respect to FIG. 2.

An operating system 230 includes procedures for handling various basic system services and for performing hardware dependent tasks.

In some implementations, a data obtainer 242 is configured to obtain data (e.g., captured image frames of the physical environment 105, presentation data, input data, user interaction data, camera pose tracking information, eye tracking information, head/body pose tracking information, hand/limb/finger/extremity tracking information, sensor data, location data, etc.) from at least one of the I/O devices 206 of the controller 110, the I/O devices and sensors 306 of the electronic device 120, and the optional remote input devices. To that end, in various implementations, the data obtainer 242 includes instructions and/or logic therefor, and heuristics and metadata therefor.

In some implementations, a mapper and locator engine 244 is configured to map the physical environment 105 and to track the position/location of at least the electronic device 120 or the user 150 with respect to the physical environment 105. To that end, in various implementations, the mapper and locator engine 244 includes instructions and/or logic therefor, and heuristics and metadata therefor.

In some implementations, a data transmitter 246 is configured to transmit data (e.g., presentation data such as rendered image frames associated with the XR environment, location data, etc.) to at least the electronic device 120 and optionally one or more other devices. To that end, in various implementations, the data transmitter 246 includes instructions and/or logic therefor, and heuristics and metadata therefor.

In some implementations, a privacy architecture 408 is configured to ingest data and filter user information and/or identifying information within the data based on one or more privacy filters. The privacy architecture 408 is described in more detail below with reference to FIG. 4A. To that end, in various implementations, the privacy architecture 408 includes instructions and/or logic therefor, and heuristics and metadata therefor.

In some implementations, a motion state estimator 410 is configured to obtain (e.g., receive, retrieve, or determine/generate) a motion state vector 411 associated with the electronic device 120 (and the user 150) (e.g., including a current motion state associated with the electronic device 120) based on input data and update the motion state vector 411 over time. For example, as shown in FIG. 4B, the motion state vector 411 includes a motion state descriptor 422 for the electronic device 120 (e.g., stationary, in-motion, walking, running, cycling, operating or riding in an automobile car, operating or riding in a boat, operating or riding in a bus, operating or riding in a train, operating or riding in an aircraft, or the like), translational movement values 424 associated with the electronic device 120 (e.g., a heading, a velocity value, an acceleration value, etc.), angular movement values 426 associated with the electronic device 120 (e.g., an angular velocity value, an angular acceleration value, and/or the like for each of the pitch, roll, and yaw dimensions), and/or the like. The motion state estimator 410 is described in more detail below with reference to FIG. 4A. To that end, in various implementations, the motion state estimator 410 includes instructions and/or logic therefor, and heuristics and metadata therefor.

In some implementations, an eye tracking engine 412 is configured to obtain (e.g., receive, retrieve, or determine/generate) an eye tracking vector 413 as shown in FIG. 4B (e.g., with a gaze direction) based on the input data and update the eye tracking vector 413 over time. For example, the gaze direction indicates a point (e.g., associated with x, y, and z coordinates relative to the physical environment 105 or the world-at-large), a physical object, or a region of interest (ROI) in the physical environment 105 at which the user 150 is currently looking. As another example, the gaze direction indicates a point (e.g., associated with x, y, and z coordinates relative to the XR environment 128), an XR object, or a ROI in the XR environment 128 at which the user 150 is currently looking. The eye tracking engine 412 is described in more detail below with reference to FIG. 4A. To that end, in various implementations, the eye tracking engine 412 includes instructions and/or logic therefor, and heuristics and metadata therefor.

In some implementations, a head/body pose tracking engine 414 is configured to obtain (e.g., receive, retrieve, or determine/generate) a pose characterization vector 415 based on the input data and update the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like. The head/body pose tracking engine 414 is described in more detail below with reference to FIG. 4A. To that end, in various implementations, the head/body pose tracking engine 414 includes instructions and/or logic therefor, and heuristics and metadata therefor. In some implementations, the motion state estimator 410, the eye tracking engine 412, and the head/body pose tracking engine 414 may be located on the electronic device 120 in addition to or in place of the controller 110.

In some implementations, a content selector 522 is configured to select XR content (sometimes also referred to herein as "graphical content" or "virtual content") from a content library 525 based on one or more user requests and/or inputs (e.g., a voice command, a selection from a user interface (UI) menu of XR content items or virtual agents (VAs), and/or the like). The content selector 522 is described in more detail below with reference to FIG. 4A. To that end, in various implementations, the content selector 522 includes instructions and/or logic therefor, and heuristics and metadata therefor.

In some implementations, a content library 525 includes a plurality of content items such as audio/visual (A/V) content, virtual agents (VAs), and/or XR content, objects, items, scenery, etc. As one example, the XR content includes 3D reconstructions of user captured videos, movies, TV episodes, and/or other XR content. In some implementations, the content library 525 is pre-populated or manually authored by the user 150. In some implementations, the content library 525 is located local relative to the controller 110. In some implementations, the content library 525 is located remote from the controller 110 (e.g., at a remote server, a cloud server, or the like).

Figure 4A:
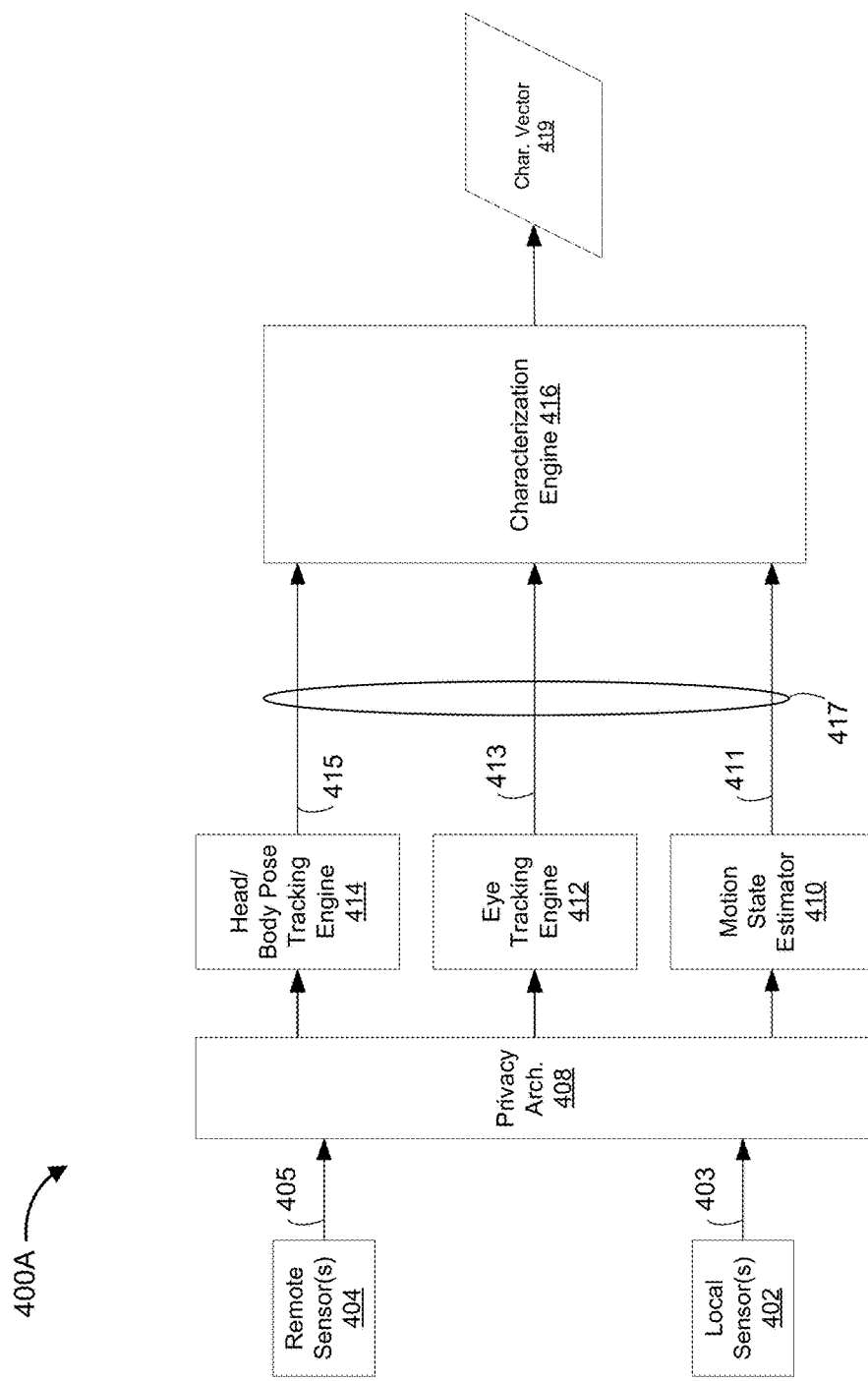
FIG. 4A is a block diagram of a first portion of a data processing architecture in accordance with some implementations.
Figure 4B:
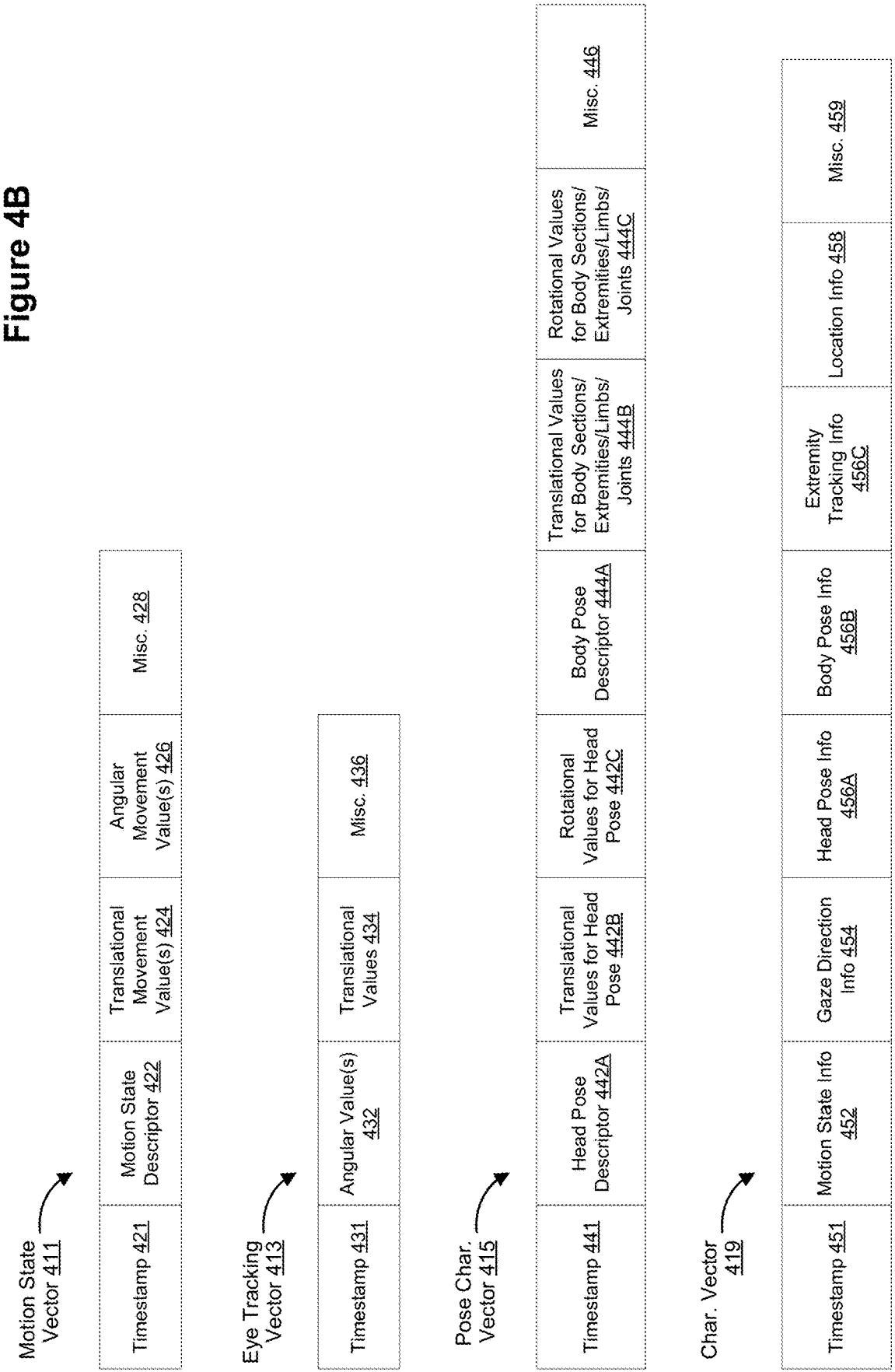
FIG. 4B illustrates example data structures in accordance with some implementations.

In some implementations, a characterization engine 416 is configured to determine/generate a characterization vector 419 based on at least one of the motion state vector 411, the eye tracking vector 413, and the pose characterization vector 415 as shown in FIG. 4A. In some implementations, the characterization engine 416 is also configured to update the pose characterization vector 419 over time. As shown in FIG. 4B, the characterization vector 419 includes motion state information 452, gaze direction information 454, head pose information 456A, body pose information 456AB, extremity tracking information 456AC, location information 458, and/or the like. The characterization engine 416 is described in more detail below with reference to FIG. 4A. To that end, in various implementations, the characterization engine 416 includes instructions and/or logic therefor, and heuristics and metadata therefor.

Figure 4C:
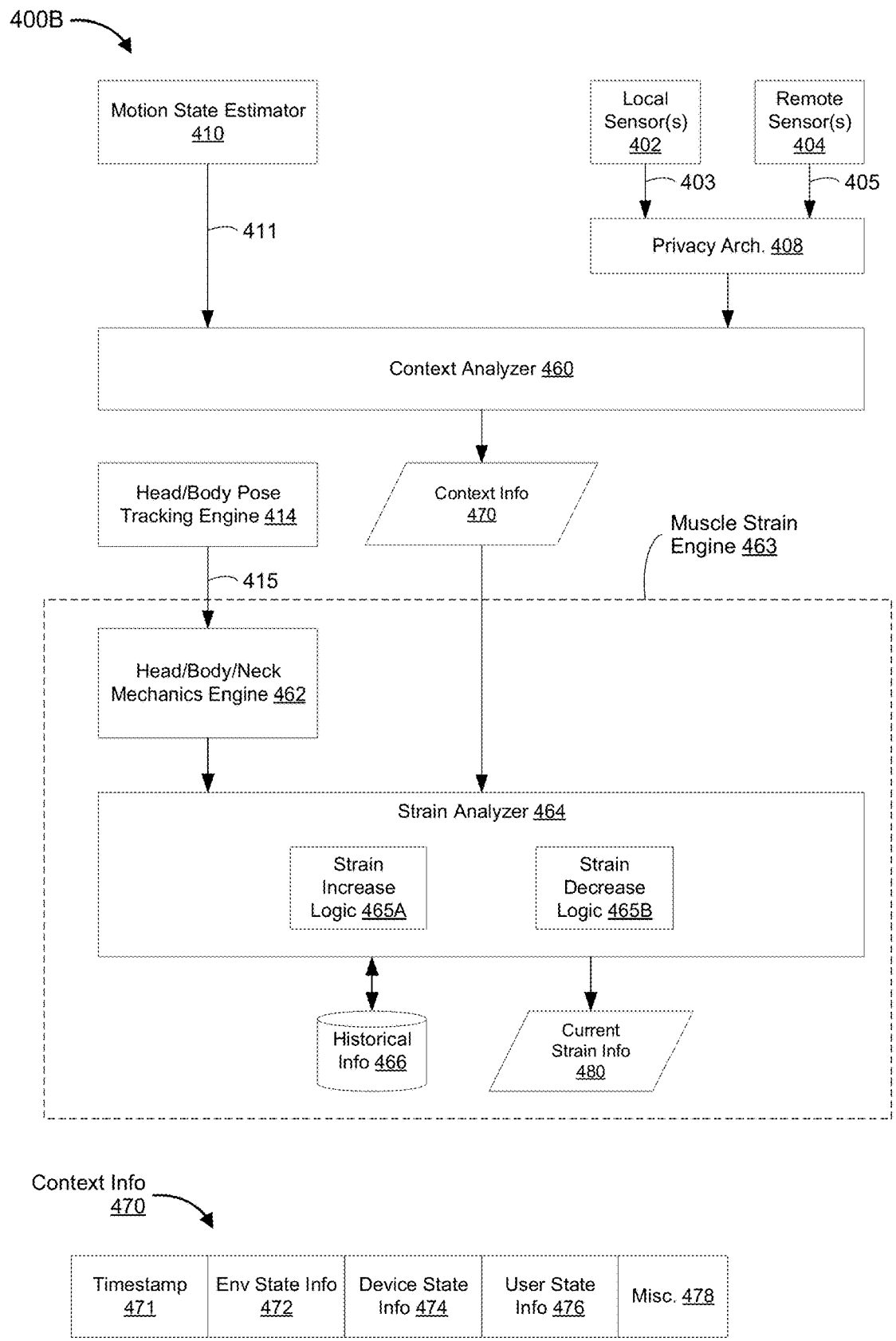
FIG. 4C is a block diagram of a second portion of a data processing architecture in accordance with some implementations.

In some implementations, a context analyzer 460 is configured to obtain (e.g., receive, retrieve, or determine/generate) a context information vector 470 based on input data shown in FIG. 4C and update the context information vector 470 over time. As shown in FIG. 4C, the context information vector 470 includes environmental state information 472, device state information 474, and user state information 476. The context analyzer 460 is described in more detail below with reference to FIG. 4C. To that end, in various implementations, the context analyzer 460 includes instructions and/or logic therefor, and heuristics and metadata therefor.

Figure 4D:
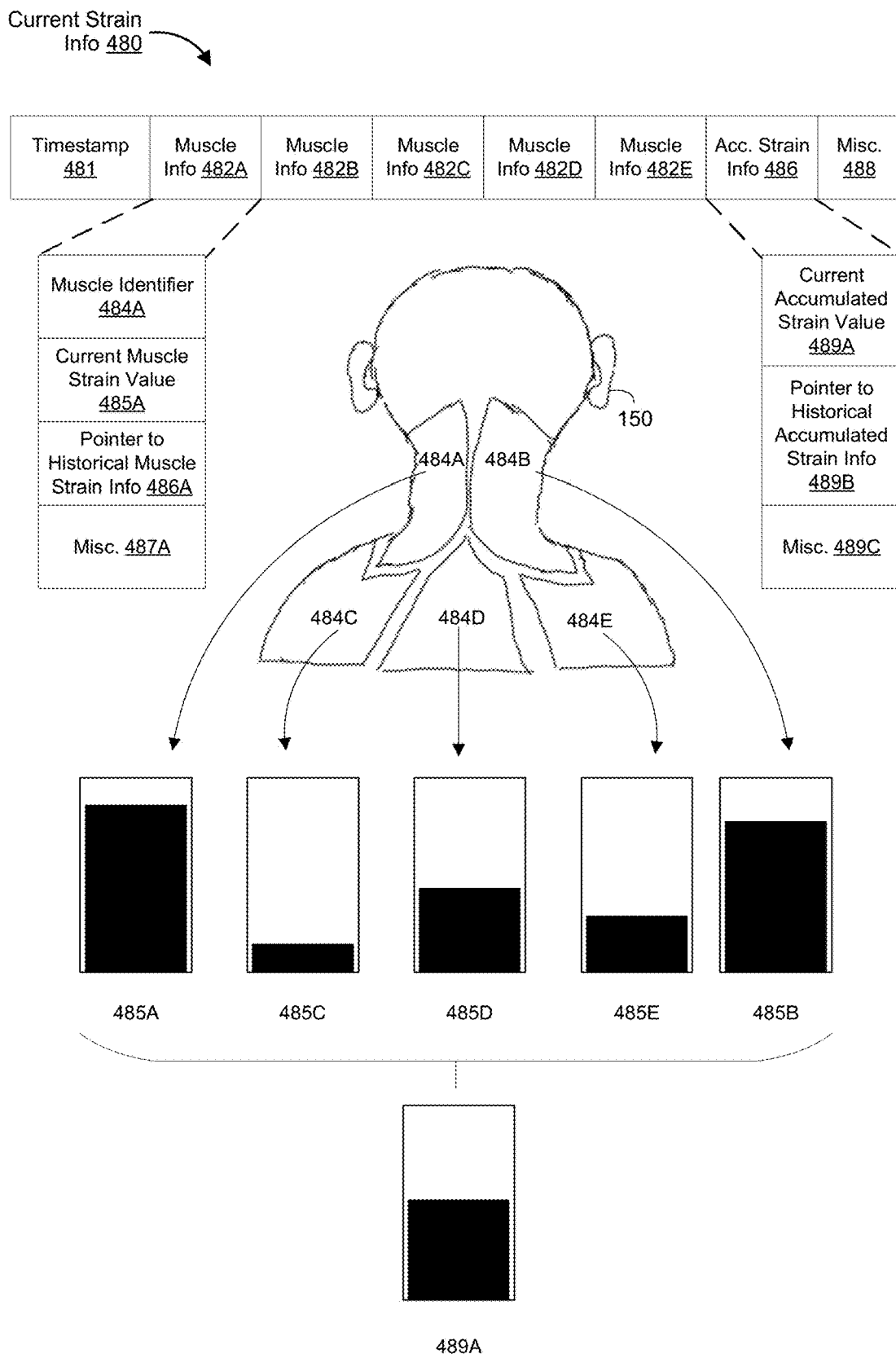
FIG. 4D illustrates example data structures in accordance with some implementations.

In some implementations, a muscle strain engine 463 is configured to obtain (e.g., receive, retrieve, or determine/generate) current strain information 480 based on input data shown in FIG. 4C and update the current strain information 480 over time. As shown in FIG. 4D, the current strain information 480 includes: muscle information 482A associated with a first muscle or muscle group/region; muscle information 482B associated with a second muscle or muscle group/region; muscle information 482C associated with a third muscle or muscle group/region; muscle information 482D associated with a fourth muscle or muscle group/region; muscle information 482E associated with a fifth muscle or muscle group/region; and current accumulated strain information 486. To that end, in various implementations, the muscle strain engine 463 includes a head/body/neck mechanics engine 462 and a strain analyzer 464 with strain increase logic 465A and strain decrease logic 465B. The muscle strain engine 463 is described in more detail below with reference to FIG. 4C. To that end, in various implementations, the muscle strain engine 463 includes instructions and/or logic therefor, and heuristics and metadata therefor.

In some implementations, a posture summary engine 468A is configured to generate and surface a notification that corresponds to a posture summary for a user. In some implementations, the posture summary engine 468A is also configured to generate accumulated strain visualizations 469 including an animation of a representation of the user over the respective time window that corresponds to one or more instances in which head pose information changes associated with the user caused an increase or a decrease to the accumulated strain value greater than a significance threshold. The posture summary engine 468A is described in more detail below with reference to FIG. 4E. To that end, in various implementations, the posture summary engine 468A includes instructions and/or logic therefor, and heuristics and metadata therefor.

In some implementations, an application programing interface (API) 468B is configured to provide access to the current strain information 480 to at least one of: the operating system of the controller 110, the electronic device 120, or a combination thereof; third-party programs or applications; and/or the like. As such, the current strain information 480 may be used in various downstream processes. The API 468B is described in more detail below with reference to FIG. 4E. To that end, in various implementations, the API 468B includes instructions and/or logic therefor, and heuristics and metadata therefor.

In some implementations, a content manager 530 is configured to manage and update the layout, setup, structure, and/or the like for the XR environment 128 including one or more of VA(s), XR content, one or more user interface (UI) elements associated with the XR content, and/or the like. The content manager 530 is described in more detail below with reference to FIG. 5. To that end, in various implementations, the content manager 530 includes instructions and/or logic therefor, and heuristics and metadata therefor. In some implementations, the content manager 530 includes a frame buffer 532, a content updater 534, and a feedback engine 536. In some implementations, the frame buffer 532 includes XR content, a rendered image frame, and/or the like for one or more past instances and/or frames.

In some implementations, the content updater 534 is configured to modify the XR environment 128 over time based on translational or rotational movement of the electronic device 120 or physical objects within the physical environment 105, user inputs (e.g., a change in context, hand/extremity tracking inputs, eye tracking inputs, touch inputs, voice commands, modification/manipulation inputs with the physical object, and/or the like), and/or the like. To that end, in various implementations, the content updater 534 includes instructions and/or logic therefor, and heuristics and metadata therefor.

In some implementations, the feedback engine 536 is configured to generate sensory feedback (e.g., visual feedback such as text or lighting changes, audio feedback, haptic feedback, etc.) associated with the XR environment 128. To that end, in various implementations, the feedback engine 536 includes instructions and/or logic therefor, and heuristics and metadata therefor.

In some implementations, a rendering engine 550 is configured to render a graphical user interface (GUI) or an XR environment 128 (sometimes also referred to herein as a "graphical environment" or "virtual environment") or image frame associated therewith as well as accumulated strain visualizations 469, VA(s), XR content, one or more UI elements associated with the XR content, and/or the like. To that end, in various implementations, the rendering engine 550 includes instructions and/or logic therefor, and heuristics and metadata therefor. In some implementations, the rendering engine 550 includes a pose determiner 552, a renderer 554, an optional image processing architecture 556, and an optional compositor 558. One of ordinary skill in the art will appreciate that the optional image processing architecture 556 and the optional compositor 558 may be present for video pass-through configurations but may be removed for fully VR or optical see-through configurations.

In some implementations, the pose determiner 552 is configured to determine a current camera pose of the electronic device 120 and/or the user 150 relative to the A/V content and/or XR content. The pose determiner 552 is described in more detail below with reference to FIG. 5. To that end, in various implementations, the pose determiner 552 includes instructions and/or logic therefor, and heuristics and metadata therefor.

In some implementations, the renderer 554 is configured to render the accumulated strain visualizations 469. In some implementations, the renderer 554 is configured to render the A/V content and/or the XR content according to the current camera pose relative thereto. The renderer 554 is described in more detail below with reference to FIG. 5. To that end, in various implementations, the renderer 554 includes instructions and/or logic therefor, and heuristics and metadata therefor.

In some implementations, the image processing architecture 556 is configured to obtain (e.g., receive, retrieve, or capture) an image stream including one or more images of the physical environment 105 from the current camera pose of the electronic device 120 and/or the user 150. In some implementations, the image processing architecture 556 is also configured to perform one or more image processing operations on the image stream such as warping, color correction, gamma correction, sharpening, noise reduction, white balance, and/or the like. The image processing architecture 556 is described in more detail below with reference to FIG. 5. To that end, in various implementations, the image processing architecture 556 includes instructions and/or logic therefor, and heuristics and metadata therefor.

In some implementations, the compositor 558 is configured to composite the rendered A/V content and/or XR content with the processed image stream of the physical environment 105 from the image processing architecture 556 to produce rendered image frames of the XR environment 128 for display. The compositor 558 is described in more detail below with reference to FIG. 5. To that end, in various implementations, the compositor 558 includes instructions and/or logic therefor, and heuristics and metadata therefor.

Although the data obtainer 242, the mapper and locator engine 244, the data transmitter 246, the privacy architecture 408, the motion state estimator 410, the eye tracking engine 412, the head/body pose tracking engine 414, the characterization engine 416, the context analyzer 460, the muscle strain engine 463, the posture summary engine 468A, the API 468B, the content selector 522, the content manager 530, and the rendering engine 550 are shown as residing on a single device (e.g., the controller 110), it should be understood that in other implementations, any combination of the data obtainer 242, the mapper and locator engine 244, the data transmitter 246, the privacy architecture 408, the motion state estimator 410, the eye tracking engine 412, the head/body pose tracking engine 414, the characterization engine 416, the context analyzer 460, the muscle strain engine 463, the posture summary engine 468A, the API 468B, the content selector 522, the content manager 530, and the rendering engine 550 may be located in separate computing devices.

In some implementations, the functions and/or components of the controller 110 are combined with or provided by the electronic device 120 shown below in FIG. 3. Moreover, FIG. 2 is intended more as a functional description of the various features which may be present in a particular implementation as opposed to a structural schematic of the implementations described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 3:
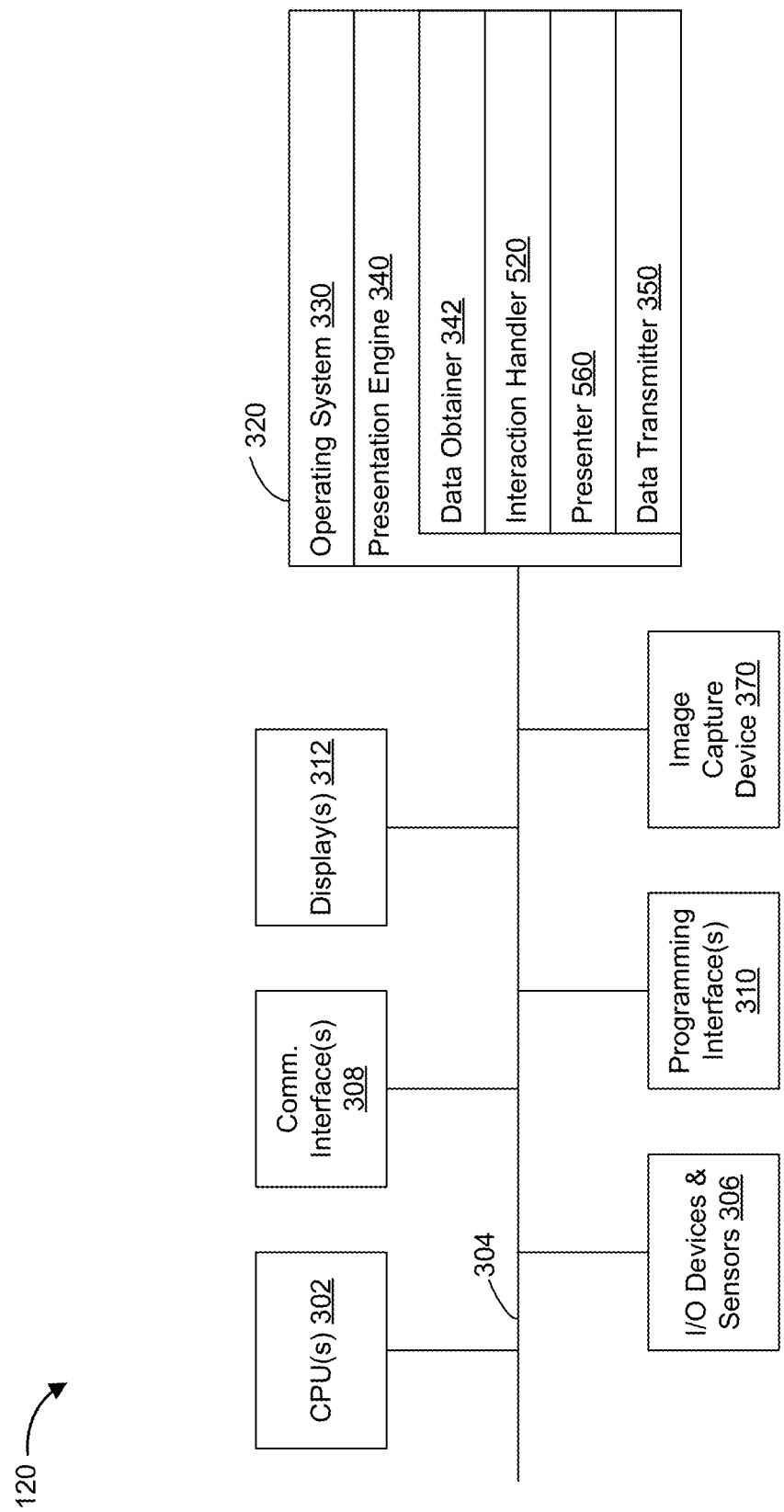
FIG. 3 is a block diagram of an example electronic device in accordance with some implementations.

FIG. 3 is a block diagram of an example of the electronic device 120 (e.g., a mobile phone, tablet, laptop, near-eye system, wearable computing device, or the like) in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the electronic device 120 includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 310, one or more displays 312, an image capture device 370 (e.g., one or more optional interior-facing and/or exterior-facing image sensors), a memory 320, and one or more communication buses 304 for interconnecting these and various other components.

In some implementations, the one or more communication buses 304 include circuitry that interconnects and controls communications between system components. In some implementations, the one or more I/O devices and sensors 306 include at least one of an inertial measurement unit (IMU), an accelerometer, a gyroscope, a magnetometer, a thermometer, one or more physiological sensors (e.g., blood pressure monitor, heart rate monitor, blood oximetry monitor, blood glucose monitor, etc.), one or more microphones, one or more speakers, a haptics engine, a heating and/or cooling unit, a skin shear engine, one or more depth sensors (e.g., structured light, time-of-flight, LiDAR, or the like), a localization and mapping engine, an eye tracking engine, a head/body pose tracking engine, a hand/limb/finger/extremity tracking engine, a camera pose tracking engine, and/or the like.

In some implementations, the one or more displays 312 are configured to present the XR environment to the user. In some implementations, the one or more displays 312 are also configured to present flat video content to the user (e.g., a 2-dimensional or "flat" AVI, FLV, WMV, MOV, MP4, or the like file associated with a TV episode or a movie, or live video pass-through of the physical environment 105). In some implementations, the one or more displays 312 correspond to touchscreen displays (e.g., similar to the display 122 in FIG. 1). In some implementations, the one or more displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more displays 312 correspond to diffractive, reflective, polarized, holographic, etc. waveguide displays. For example, the electronic device 120 includes a single display such as the display 122. In another example, the electronic device 120 includes a display for each eye of the user. In some implementations, the one or more displays 312 are capable of presenting AR and VR content. In some implementations, the one or more displays 312 are capable of presenting AR or VR content.

In some implementations, the image capture device 370 correspond to one or more RGB cameras (e.g., with a complementary metal-oxide-semiconductor (CMOS) image sensor or a charge-coupled device (CCD) image sensor), IR image sensors, event-based cameras, and/or the like. In some implementations, the image capture device 370 includes a lens assembly, a photodiode, and a front-end architecture. In some implementations, the image capture device 370 includes exterior-facing and/or interior-facing image sensors.

The memory 320 includes high-speed random-access memory, such as DRAM, SRAM, DDR RAM, or other random-access solid-state memory devices. In some implementations, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some implementations, the memory 320 or the non-transitory computer readable storage medium of the memory 320 stores the following programs, modules and data structures, or a subset thereof including an optional operating system 330 and a presentation engine 340.

The operating system 330 includes procedures for handling various basic system services and for performing hardware dependent tasks. In some implementations, the presentation engine 340 is configured to present media items and/or XR content to the user via the one or more displays 312. To that end, in various implementations, the presentation engine 340 includes a data obtainer 342, an interaction handler 520, a presenter 560, and a data transmitter 350.

In some implementations, the data obtainer 342 is configured to obtain data (e.g., presentation data such as rendered image frames associated with the user interface or the XR environment, input data, user interaction data, head tracking information, camera pose tracking information, eye tracking information, hand/limb/finger/extremity tracking information, sensor data, location data, etc.) from at least one of the I/O devices and sensors 306 of the electronic device 120, the controller 110, and the remote input devices. To that end, in various implementations, the data obtainer 342 includes instructions and/or logic therefor, and heuristics and metadata therefor.

In some implementations, the interaction handler 520 is configured to detect user interactions (e.g., gestural inputs detected via hand/extremity tracking, eye gaze inputs detected via eye tracking, voice commands, etc.) with the presented A/V content and/or XR content. To that end, in various implementations, the interaction handler 520 includes instructions and/or logic therefor, and heuristics and metadata therefor.

In some implementations, the presenter 560 is configured to present and update A/V content and/or XR content (e.g., the rendered image frames associated with the GUI or the XR environment 128 including the accumulated strain visualizations 469, VA(s), the XR content, one or more UI elements associated with the XR content, and/or the like) via the one or more displays 312. To that end, in various implementations, the presenter 560 includes instructions and/or logic therefor, and heuristics and metadata therefor.

In some implementations, the data transmitter 350 is configured to transmit data (e.g., presentation data, location data, user interaction data, head tracking information, camera pose tracking information, eye tracking information, hand/limb/finger/extremity tracking information, etc.) to at least the controller 110. To that end, in various implementations, the data transmitter 350 includes instructions and/or logic therefor, and heuristics and metadata therefor.

Although the data obtainer 342, the interaction handler 520, the presenter 560, and the data transmitter 350 are shown as residing on a single device (e.g., the electronic device 120), it should be understood that in other implementations, any combination of the data obtainer 342, the interaction handler 520, the presenter 560, and the data transmitter 350 may be located in separate computing devices.

Moreover, FIG. 3 is intended more as a functional description of the various features which may be present in a particular implementation as opposed to a structural schematic of the implementations described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

FIG. 4A is a block diagram of a first portion 400A of an example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the first portion 400A of the data processing architecture is included in a computing system such as the controller 110 shown in FIGS. 1 and 2; the electronic device 120 shown in FIGS. 1 and 3; and/or a suitable combination thereof.

As shown in FIG. 4A, one or more local sensors 402 of the controller 110, the electronic device 120, and/or a combination thereof obtain local sensor data 403 associated with the physical environment 105. For example, the local sensor data 403 includes images or a stream thereof of the physical environment 105, simultaneous location and mapping (SLAM) information for the physical environment 105 and the location of the electronic device 120 or the user 150 relative to the physical environment 105, ambient lighting information for the physical environment 105, ambient audio information for the physical environment 105, acoustic information for the physical environment 105, dimensional information for the physical environment 105, semantic labels for objects within the physical environment 105, and/or the like. In some implementations, the local sensor data 403 includes un-processed or post-processed information.

Similarly, as shown in FIG. 4A, one or more remote sensors 404 associated with the optional remote input devices within the physical environment 105 obtain remote sensor data 405 associated with the physical environment 105. For example, the remote sensor data 405 includes images or a stream thereof of the physical environment 105, SLAM information for the physical environment 105 and the location of the electronic device 120 or the user 150 relative to the physical environment 105, ambient lighting information for the physical environment 105, ambient audio information for the physical environment 105, acoustic information for the physical environment 105, dimensional information for the physical environment 105, semantic labels for objects within the physical environment 105, and/or the like. In some implementations, the remote sensor data 405 includes un-processed or post-processed information.

According to some implementations, the privacy architecture 408 ingests the local sensor data 403 and the remote sensor data 405. In some implementations, the privacy architecture 408 includes one or more privacy filters associated with user information and/or identifying information. In some implementations, the privacy architecture 408 includes an opt-in feature where the electronic device 120 informs the user 150 as to what user information and/or identifying information is being monitored and how the user information and/or the identifying information will be used. In some implementations, the privacy architecture 408 selectively prevents and/or limits the data processing architecture 400A/400B/400C or portions thereof from obtaining and/or transmitting the user information. To this end, the privacy architecture 408 receives user preferences and/or selections from the user 150 in response to prompting the user 150 for the same. In some implementations, the privacy architecture 408 prevents the data processing architecture 400A/400B/400C from obtaining and/or transmitting the user information unless and until the privacy architecture 408 obtains informed consent from the user 150. In some implementations, the privacy architecture 408 anonymizes (e.g., scrambles, obscures, encrypts, and/or the like) certain types of user information. For example, the privacy architecture 408 receives user inputs designating which types of user information the privacy architecture 408 anonymizes. As another example, the privacy architecture 408 anonymizes certain types of user information likely to include sensitive and/or identifying information, independent of user designation (e.g., automatically).

According to some implementations, the motion state estimator 410 obtains the local sensor data 403 and the remote sensor data 405 after it has been subjected to the privacy architecture 408. In some implementations, the motion state estimator 410 obtains (e.g., receives, retrieves, or determines/generates) a motion state vector 411 based on the input data and updates the motion state vector 411 over time.

FIG. 4B shows an example data structure for the motion state vector 411 in accordance with some implementations. As shown in FIG. 4B, the motion state vector 411 may correspond to an N-tuple characterization vector or characterization tensor that includes a timestamp 421 (e.g., the most recent time the motion state vector 411 was updated), a motion state descriptor 422 for the electronic device 120 (e.g., stationary, in-motion, running, walking, cycling, driving or riding in a car, driving or riding in a boat, driving or riding in a bus, riding in a train, riding in a plane, or the like), translational movement values 424 associated with the electronic device 120 (e.g., a heading, a displacement value, a velocity value, an acceleration value, a jerk value, etc.), angular movement values 426 associated with the electronic device 120 (e.g., an angular displacement value, an angular velocity value, an angular acceleration value, an angular jerk value, and/or the like for each of the pitch, roll, and yaw dimensions), and/or miscellaneous information 428. One of ordinary skill in the art will appreciate that the data structure for the motion state vector 411 in FIG. 4B is merely an example that may include different information portions in various other implementations and be structured in myriad ways in various other implementations.

According to some implementations, the eye tracking engine 412 obtains the local sensor data 403 and the remote sensor data 405 after it has been subjected to the privacy architecture 408. In some implementations, the eye tracking engine 412 obtains (e.g., receives, retrieves, or determines/ generates) an eye tracking vector 413 based on the input data and updates the eye tracking vector 413 over time.

FIG. 4B shows an example data structure for the eye tracking vector 413 in accordance with some implementations. As shown in FIG. 4B, the eye tracking vector 413 may correspond to an N-tuple characterization vector or characterization tensor that includes a timestamp 431 (e.g., the most recent time the eye tracking vector 413 was updated), one or more angular values 432 for a current gaze direction (e.g., roll, pitch, and yaw values), one or more translational values 434 for the current gaze direction (e.g., x, y, and z values relative to the physical environment 105, the world-at-large, and/or the like), and/or miscellaneous information 436. One of ordinary skill in the art will appreciate that the data structure for the eye tracking vector 413 in FIG. 4B is merely an example that may include different information portions in various other implementations and be structured in myriad ways in various other implementations.

For example, the gaze direction indicates a point (e.g., associated with x, y, and z coordinates relative to the physical environment 105 or the world-at-large), a physical object, or a region of interest (ROI) in the physical environment 105 at which the user 150 is currently looking. As another example, the gaze direction indicates a point (e.g., associated with x, y, and z coordinates relative to the XR environment 128), an XR object, or a region of interest (ROI) in the XR environment 128 at which the user 150 is currently looking.

According to some implementations, the head/body pose tracking engine 414 obtains the local sensor data 403 and the remote sensor data 405 after it has been subjected to the privacy architecture 408. In some implementations, the head/body pose tracking engine 414 obtains (e.g., receives, retrieves, or determines/generates) a pose characterization vector 415 based on the input data and updates the pose characterization vector 415 over time.

FIG. 4B shows an example data structure for the pose characterization vector 415 in accordance with some implementations. As shown in FIG. 4B, the pose characterization vector 415 may correspond to an N-tuple characterization vector or characterization tensor that includes a timestamp 441 (e.g., the most recent time the pose characterization vector 415 was updated), a head pose descriptor 442A (e.g., upward, downward, neutral, etc.), translational values for the head pose 442B, rotational values for the head pose 442C, a body pose descriptor 444A (e.g., standing, sitting, prone, etc.), translational values for body sections/extremities/limbs/joints 444B, rotational values for the body sections/extremities/limbs/joints 444C, and/or miscellaneous information 446. In some implementations, the pose characterization vector 415 also includes information associated with finger/hand/extremity tracking. One of ordinary skill in the art will appreciate that the data structure for the pose characterization vector 415 in FIG. 4B is merely an example that may include different information portions in various other implementations and be structured in myriad ways in various other implementations. According to some implementations, the motion state vector 411, the eye tracking vector 413 and the pose characterization vector 415 are collectively referred to as an input vector 417.

According to some implementations, the characterization engine 416 obtains the motion state vector 411, the eye tracking vector 413 and the pose characterization vector 415. In some implementations, the characterization engine 416 obtains (e.g., receives, retrieves, or determines/generates) the characterization vector 419 based on the motion state vector 411, the eye tracking vector 413, and the pose characterization vector 415.

FIG. 4B shows an example data structure for the characterization vector 419 in accordance with some implementations. As shown in FIG. 4B, the characterization vector 419 may correspond to an N-tuple characterization vector or characterization tensor that includes a timestamp 451 (e.g., the most recent time the characterization vector 419 was updated), motion state information 452 (e.g., the motion state descriptor 422), gaze direction information 454 (e.g., a function of the one or more angular values 432 and the one or more translational values 434 within the eye tracking vector 413), head pose information 456A (e.g., a function of the head pose descriptor 442A within the pose characterization vector 415), body pose information 456B (e.g., a function of the body pose descriptor 444A within the pose characterization vector 415), extremity tracking information 456C (e.g., a function of the body pose descriptor 444A within the pose characterization vector 415 that is associated with extremities of the user 150 that are being tracked by the controller 110, the electronic device 120, and/or a combination thereof), location information 458 (e.g., a household location such as a kitchen or living room, a vehicular location such as an automobile, plane, etc., and/or the like), and/or miscellaneous information 459.

FIG. 4C is a block diagram of a second portion 400B of the example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the second portion 400B of the data processing architecture is included in a computing system such as the controller 110 shown in FIGS. 1 and 2; the electronic device 120 shown in FIGS. 1 and 3; and/or a suitable combination thereof. FIG. 4C is similar to and adapted from FIG. 4A. Therefore, similar reference numbers are used in FIGS. 4A and 4C. As such, only the differences between FIGS. 4A and 4C will be described below for the sake of brevity.

According to some implementations, the context analyzer 460 obtains the motion state vector 411 from the motion state estimator 410. As shown in FIG. 4C, the context analyzer 460 also obtains the local sensor data 403 and the remote sensor data 405 after being subjected to the privacy architecture 408.

In some implementations, the context analyzer 460 obtains (e.g., receives, retrieves, or determines/generates) a context information vector 470 based on the input data and updates the context information vector 470 over time. FIG. 4C shows an example data structure for the context information vector 470 in accordance with some implementations. As shown in FIG. 4C, the context information vector 470 may correspond to an N-tuple characterization vector or characterization tensor that includes: a timestamp 471 (e.g., the most recent time the context information vector 470 was updated); environmental state information 472 associated with a current state of the physical environment 105 (e.g., ambient temperature information, ambient humidity information, ambient lighting information, ambient audio information, semantic labels for physical objects within the physical environment 105, locations for physical objects within the physical environment 105, etc.); device state information 474 associated with a current state of the controller 110, the electronic device 120, or a combination thereof, or the like (e.g., current foreground applications, current background applications, power/charge remaining, device temperature metrics, resource consumption metrics (e.g., CPU, RAM, storage, network I/O, etc.), etc.); user state information 476 associated with a current state of the user 150 (e.g., the characterization vector 419, physiological information associated with the user 150, the motion state descriptor 42, etc.); and miscellaneous information 478. One of ordinary skill in the art will appreciate that the data structure for the context information vector 470 in FIG. 4C is merely an example that may include different information portions in various other implementations and be structured in myriad ways in various other implementations.

According to some implementations, the head/body/neck mechanics engine 462 obtains (e.g., receives, retrieves, or determines/generates) displacement, velocity, acceleration, jerk, torque, etc. values for the head/body/neck of the user 150 based on changes to the pose characterization vector 415. In some implementations, the strain analyzer 464 determines current strain information 480 for one or more muscles or muscle groups based on: the displacement, velocity, acceleration, jerk, torque, etc. values for the head/body/neck of the user 150 from the head/body/neck mechanics engine 462; historical information 466; and the context information vector 470. In some implementations, the strain analyzer 464 determines the current strain information 480 based on strain increase logic 465A and/or strain decrease logic 465B. In some implementations, the historical information 466 corresponds to local or remote storage repository, including: strain information for one or more previous time periods on an overall basis, individual muscle or muscle group/region basis, etc.; context information for one or more previous time periods; and/or displacement, velocity, acceleration, jerk, torque, etc. values for the head/body/neck of the user 150 for one or more previous time periods.

FIG. 4D shows an example data structure for the current strain information 480 in accordance with some implementations. As shown in FIG. 4C, the current strain information 480 may correspond to an N-tuple characterization vector or characterization tensor that includes: a timestamp 481; muscle information 482A associated with a first muscle or muscle group/region; muscle information 482B associated with a second muscle or muscle group/region; muscle information 482C associated with a third muscle or muscle group/region; muscle information 482D associated with a fourth muscle or muscle group/region; muscle information 482E associated with a fifth muscle or muscle group/region; accumulated strain information 486 associated with a function of the muscle information 482A-482E; and miscellaneous information 488. One of ordinary skill in the art will appreciate that the data structure for current strain information 480 in FIG. 4D is merely an example that may include different information portions in various other implementations and be structured in myriad ways in various other implementations.

As shown in FIG. 4D, the muscle information 482A for the first muscle or muscle group/region includes: a muscle identifier 484A for the first muscle or muscle group/region (e.g., a unique identifier, a label, a name, or the like for the first muscle or muscle group/region); a current muscle strain value 485A for the first muscle or muscle group/region; a pointer to historical muscle strain information 486A for the first muscle or muscle group/region within the historical information 466; and miscellaneous information 487A associated with the first muscle or muscle group/region.

As shown in FIG. 4D, for example, the muscle strain engine 463 determines current muscle strain values 485A, 485B, 485C, 485D, and 485E for muscles or muscle groups/regions 484A, 484B, 484C, 484D, and 484E, respectively, of the user 150. Furthermore, the muscle strain engine 463 updates (increases or decreases) the muscle strain values 485A, 485B, 485C, 485D, and 485E over time based on rotational and/or translational movement of the user 150 that triggers the strain increase logic 465A and/or the strain decrease logic 465B.

As shown in FIG. 4D, the accumulated strain information 486: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information 486. As shown in FIG. 4D, for example, the muscle strain engine 463 also determines a current accumulated strain value 489A and updates (increases or decreases) the current accumulated strain value 489A over time based on rotational and/or translational movement of the user 150 that triggers the strain increase logic 465A and/or the strain decrease logic 465B. As such, according to some implementations, the muscle strain engine 463 tracks strain values on an individual muscle or muscle group/region basis (e.g., the muscle information 482A-482E) as well as an overall strain value (e.g., the current accumulated strain information 486).

Figure 4E:
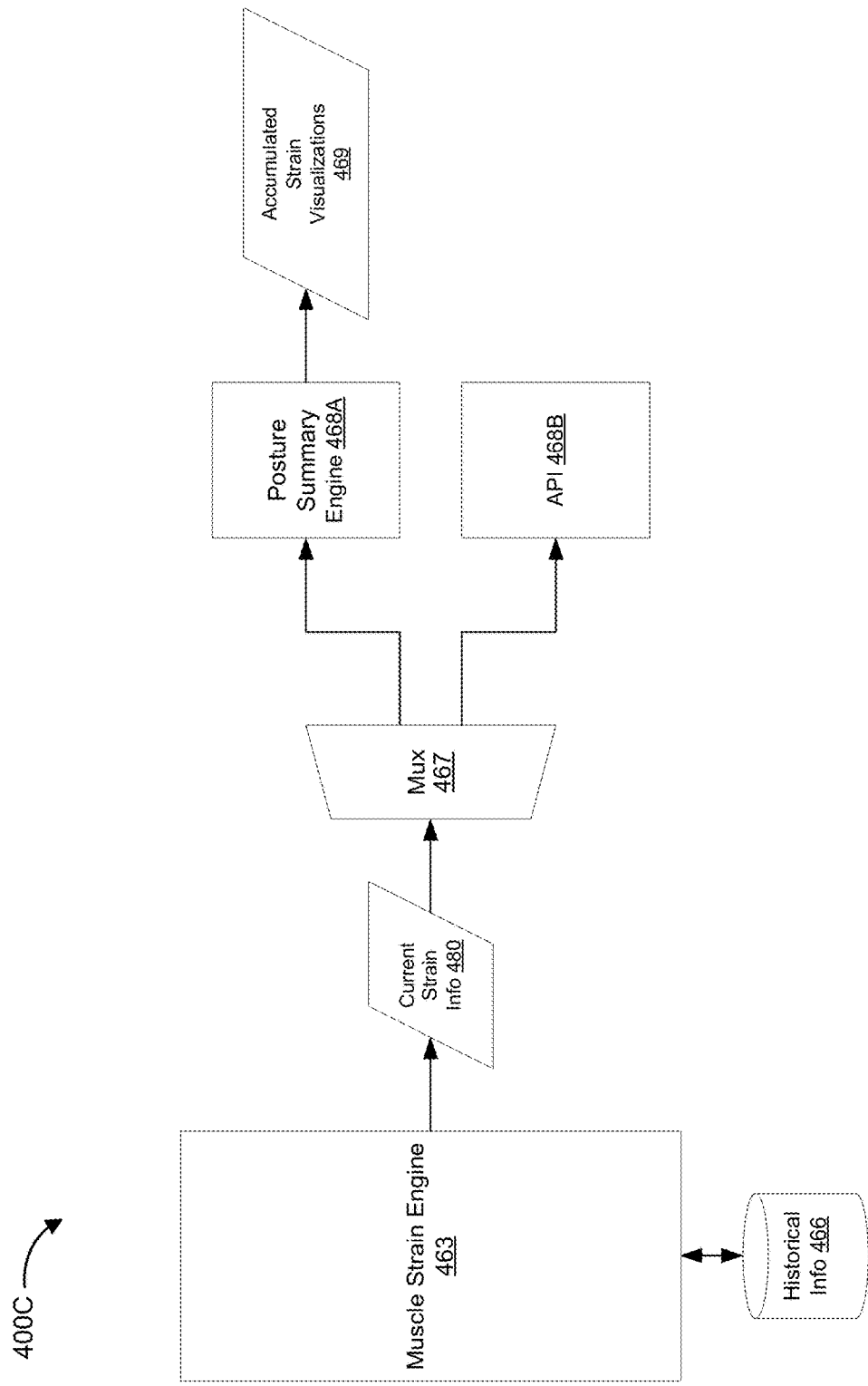
FIG. 4E is a block diagram of a third portion of a data processing architecture in accordance with some implementations.

FIG. 4E is a block diagram of a third portion 400C of the example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the third portion 400C of the example data processing architecture is included in a computing system such as the controller 110 shown in FIGS. 1 and 2; the electronic device 120 shown in FIGS. 1 and 3; and/or a suitable combination thereof. FIG. 4E is similar to and adapted from FIGS. 4A and 4C. Therefore, similar reference numbers are used in FIGS. 4A and 4C. As such, only the differences between FIGS. 4A, 4C, and 4E will be described below for the sake of brevity.

As described above with respect to FIG. 4C, the muscle strain engine 463 determines a current strain information 480. As illustrated in FIG. 4E, the current strain information 480 is provided to a multiplexer (Mux) 467. In turn, the current strain information 480 is provided to at least one of a posture summary engine 468A and an application programming interface (API) 468B. According to some implementations, the posture summary engine 468A generates and surfaces a notification that corresponds to a posture summary for a user. In some implementations, the posture summary engine 468A also generates accumulated strain visualizations 469 including an animation of a representation of the user over the respective time window that corresponds to one or more instances in which head pose information changes associated with the user caused an increase or a decrease to the accumulated strain value greater than a significance threshold. The animation of a representation of the user over the respective time window is described in greater detail below with reference to FIGS. 6C-6F. According to some implementations, the API 468B provides access to the current strain information 480 to at least one of: the operating system of the controller 110, the electronic device 120, or a combination thereof; third-party programs or applications; and/or the like. As such, the current strain information 480 may be used in various downstream processes.

Figure 5:
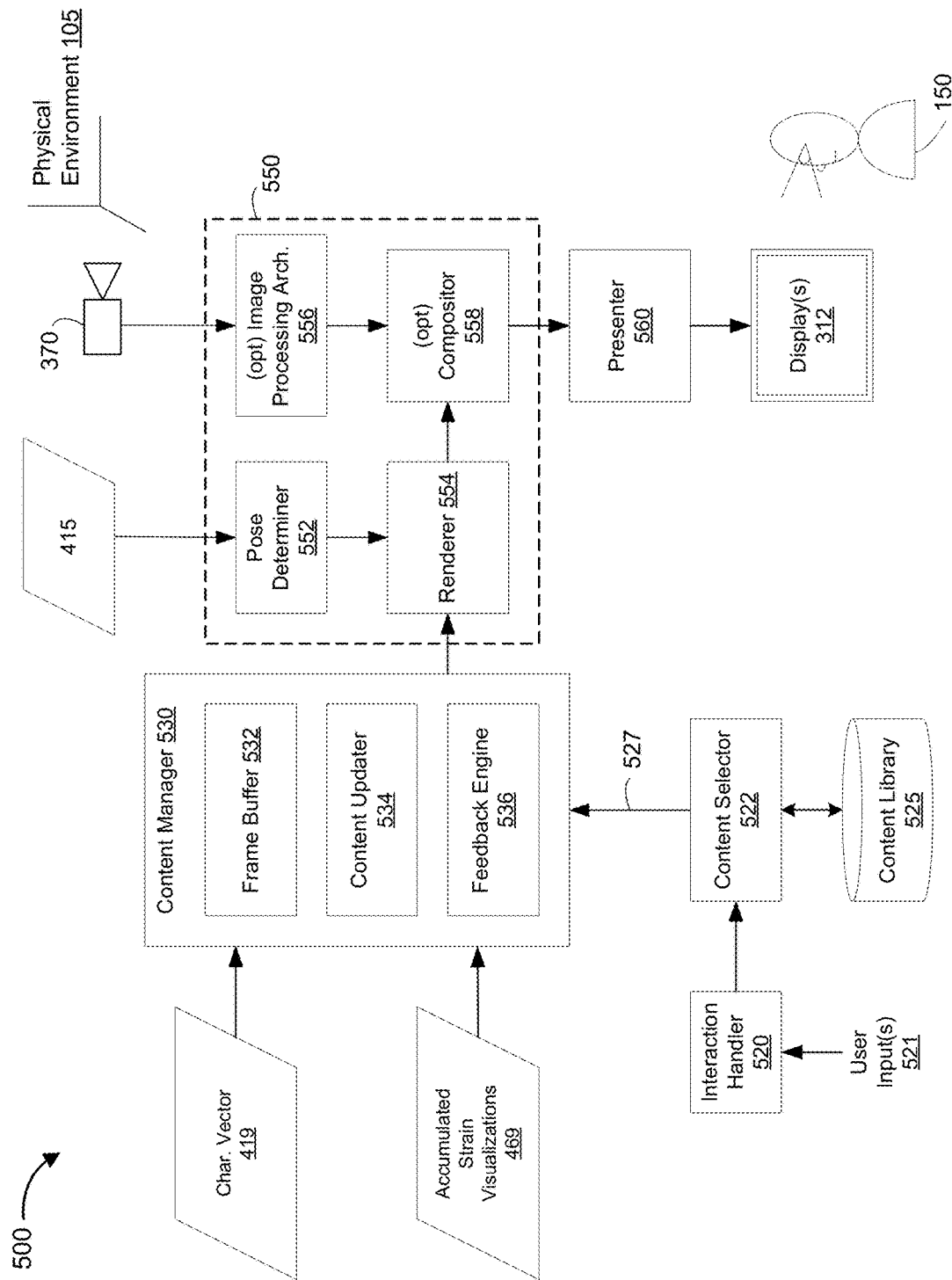
FIG. 5 is a block diagram of an example content delivery architecture in accordance with some implementations.

FIG. 5 is a block diagram of an example content delivery architecture 500 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the content delivery architecture is included in a computing system such as the controller 110 shown in FIGS. 1 and 2; the electronic device 120 shown in FIGS. 1 and 3; and/or a suitable combination thereof.

According to some implementations, the interaction handler 520 obtains (e.g., receives, retrieves, or detects) one or more user inputs 521 provided by the user 150 that are associated with selecting A/V content, one or more VAs, and/or XR content for presentation. For example, the one or more user inputs 521 correspond to a gestural input selecting XR content from a UI menu detected via hand/extremity tracking, an eye gaze input selecting XR content from the UI menu detected via eye tracking, a voice command selecting XR content from the UI menu detected via a microphone, and/or the like. In some implementations, the content selector 522 selects XR content 527 from the content library 525 based on one or more user inputs 521 (e.g., a voice command, a selection from a menu of XR content items, and/or the like).

In various implementations, the content manager 530 manages and updates the layout, setup, structure, and/or the like for the XR environment 128, including one or more of VAs, XR content, one or more UI elements associated with the XR content, and/or the like, based on the characterization vector 419, (optionally) the user inputs 521, and/or the like. To that end, the content manager 530 includes the frame buffer 532, the content updater 534, and the feedback engine 536.

In some implementations, the frame buffer 532 includes XR content, a rendered image frame, and/or the like for one or more past instances and/or frames. In some implementations, the content updater 534 modifies the XR environment 128 over time based on the characterization vector 419, the accumulated strain visualizations 469, the user inputs 521 associated with modifying and/or manipulating the XR content or VA(s), translational or rotational movement of objects within the physical environment 105, translational or rotational movement of the electronic device 120 (or the user 150), and/or the like. In some implementations, the feedback engine 536 generates sensory feedback (e.g., visual feedback such as text or lighting changes, audio feedback, haptic feedback, etc.) associated with the XR environment 128.

According to some implementations, the pose determiner 552 determines a current camera pose of the electronic device 120 and/or the user 150 relative to the XR environment 128 and/or the physical environment 105 based at least in part on the pose characterization vector 415. In some implementations, the renderer 554 renders the VA(s), the XR content 527, one or more UI elements associated with the XR content, and/or the like according to the current camera pose relative thereto.

According to some implementations, the optional image processing architecture 556 obtains an image stream from an image capture device 370 including one or more images of the physical environment 105 from the current camera pose of the electronic device 120 and/or the user 150. In some implementations, the image processing architecture 556 also performs one or more image processing operations on the image stream such as warping, color correction, gamma correction, sharpening, noise reduction, white balance, and/or the like. In some implementations, the optional compositor 558 composites the rendered XR content with the processed image stream of the physical environment 105 from the image processing architecture 556 to produce rendered image frames of the XR environment 128. In various implementations, the presenter 560 presents the rendered image frames of the XR environment 128 to the user 150 via the one or more displays 312. One of ordinary skill in the art will appreciate that the optional image processing architecture 556 and the optional compositor 558 may not be applicable for fully virtual environments (or optical see-through scenarios).

FIGS. 6A-6H illustrate a plurality of interfaces associated with surfacing accumulated strain information in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, the plurality of interfaces is rendered and presented by a computing system such as the controller 110 shown in FIGS. 1 and 2; the electronic device 120 shown in FIGS. 1 and 3; and/or a suitable combination thereof.

In some implementations, the plurality of interfaces in FIGS. 6A-6H correspond to two-dimensional (2D) graphical user interfaces (GUIs) or three-dimensional (3D) environments. In some implementations, the plurality of interfaces in FIGS. 6A-6H corresponds to the XR environment 128 shown in FIG. 1 (e.g., a 3D or volumetric user interface). As such, according to some implementations, the electronic device 120 presents the XR environment 128 to the user 150 while the user 150 is physically present within a physical environment, which is currently within the FOV 111 of an exterior-facing image sensor of the electronic device 120 (e.g., as shown in FIG. 1). In other words, in some implementations, the electronic device 120 is configured to present XR content (e.g., virtual content) and to enable optical see-through or video pass-through of at least a portion of the physical environment on the display 122. For example, the electronic device 120 corresponds to a mobile phone, tablet, laptop, near-eye system, wearable computing device, or the like. As such, in some implementations, the user 150 holds the electronic device 120 in their hand(s) similar to the operating environment 100 in FIG. 1.

Figure 6A:
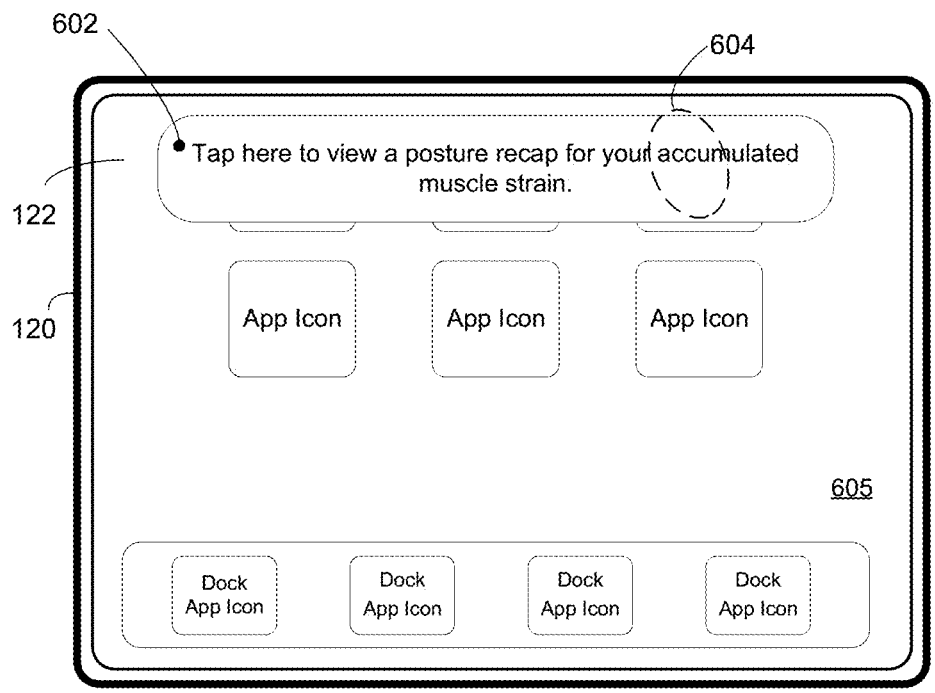
FIGS. 6A-6H illustrate a plurality of interfaces associated with surfacing accumulated strain information in accordance with some implementations.

As shown in FIG. 6A, the electronic device 120 presents a home interface 605 including a plurality of application icons and a plurality of dock application icons on the display 122. In FIG. 6A, the electronic device 120 overlays a notification 602 on the home interface 605 that corresponds to a posture summary for a user of the electronic device 120 based on accumulated muscle strain. For example, with reference to FIG. 4D, the accumulated muscle strain is based on the strain information 480, which includes a current accumulated strain value 489A associated with a function of one or more of the current muscle strain values 485A, 485B, 485C, 485D, and 485E for muscles or muscle groups/regions 484A, 484B, 484C, 484D, and 484E, respectively. For example, the electronic device 120 presents the notification 602 at a default location or in a default manner in FIG. 6A (e.g., a pop-up notification centered within the display 122, a banner notification adjacent to the top edge of the display 122, or the like).

For example, the notification 602 corresponds to 2D content or volumetric/3D virtual content. According to some implementations, the notification 602 acts as an affordance that may be selected with a touch input, hand tracking input, gaze input, voice command, or the like. In some implementations, the electronic device 120 surfaces the notification 602 once a day, twice a day, at a user-specified time, when the accumulated strain value reaches a deterministic or non-deterministic value, or the like.

Figure 6B:
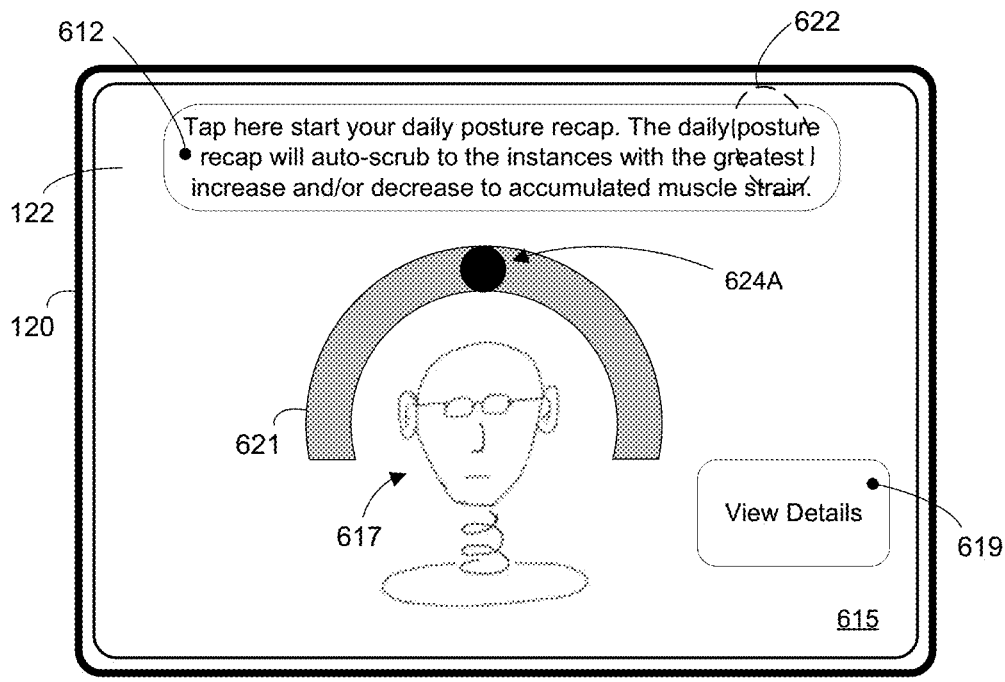

As shown in FIG. 6A, the electronic device 120 detects a first user input 604 (e.g., tap input, touch input, or the like) directed to the notification 602 (e.g., via the display 122—a touchscreen). As shown in FIG. 6B, in response to detecting the first user input 604 directed to the notification 602 in FIG. 6A, the electronic device 120 presents a posture summary interface 615 on the display. One of ordinary skill in the art will appreciate that the posture summary interface 615 may be formatted or structured in myriad ways in various other implementations.

As shown in FIG. 6B, the posture summary interface 615 includes a representation of the user 617 such as an avatar with a face modeled on the user of the electronic device 120. As shown in FIG. 6B, the posture summary interface 615 also includes a visualization of the accumulated strain 621 for the user of the electronic device 120 with a current accumulated strain value indicator 624A. As mentioned above, the accumulated (muscle) strain is based on the strain information 480, which includes a current accumulated strain value 489A (e.g., associated with the current accumulated strain value indicator 624A) corresponding to a function of one or more of the current muscle strain values 485A, 485B, 485C, 485D, and 485E for muscles or muscle groups/regions 484A, 484B, 484C, 484D, and 484E, respectively, of the user 150 (e.g., as shown in FIG. 4D).

For example, the visualization of the accumulated strain 621 corresponds to a colored gradient, wherein the wavelength of the colored gradient is based on the magnitude of the current accumulated strain value indicator 624A. According to some implementations, the wavelength of the colored gradient changes from green to red as the accumulated neck strain increases. In some implementations, the opposite occurs as the accumulated neck strain decreases.

As shown in FIG. 6B, the posture summary interface 615 further includes a first affordance 612 for initiating an animated posture summary associated with the accumulated strain for the user over a respective time window. One of ordinary skill in the art will appreciate that the animated posture summary may be presented or structured in myriad ways in various other implementations. In some implementations, the respective time window corresponds to a deterministic or non-deterministic length of time such as the last week, the last X days, the last day, the last Y hours, the last hour, the last Z minutes, workday, workout session, or the like. As such, for example, each of the T1-T6 indicators shown on the timeline in FIGS. 6C-6F corresponds to a day, Y hours, one hour, Z minutes, or the like.

For example, the first affordance 612 may be selected with a touch input, hand tracking input, gaze input, voice command, or the like. As shown in FIG. 6B, the posture summary interface 615 further includes a second affordance 619 for presenting a detailed accumulated strain interface associated with the accumulated strain value for the user over at least the respective time window (e.g., shown in FIG. 6H). For example, the second affordance 619 may be selected with a touch input, hand tracking input, gaze input, voice command, or the like.

Figure 6C:
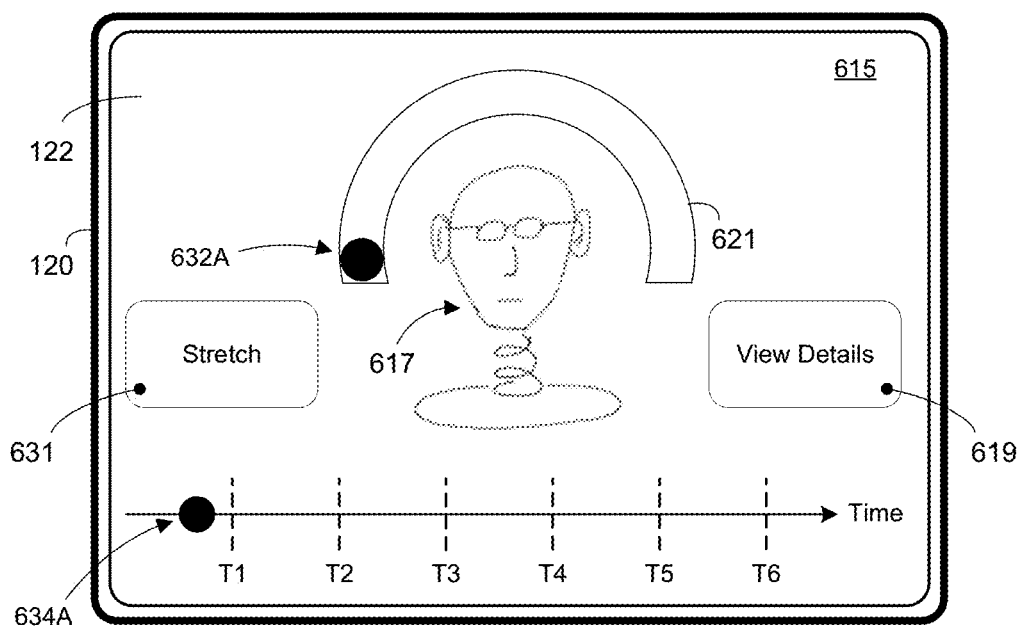

As shown in FIG. 6B, the electronic device 120 detects a second user input 622 (e.g., tap input, touch input, or the like) directed to the first affordance 612 (e.g., via the display 122—a touchscreen). As shown in FIG. 6C, in response to detecting the second user input 622 directed to the first affordance 612 in FIG. 6B, the electronic device 120 presents an animation of the representation of the user 617 over the respective time window that corresponds to one or more instances in which head pose information changes (and/or body pose information changes) associated with the user caused an increase or a decrease to the accumulated strain value greater than a significance threshold.

As shown in FIG. 6C, in response to detecting the second user input 622 directed to the first affordance 612 in FIG. 6B, the electronic device 120 ceases display of the first affordance 612 and presents a timeline with a time indicator 634A. For example, the time indicator 634A corresponds to a first instance among the one or more instances in which the head pose information changes (and/or the body pose information changes) associated with the user caused an increase or a decrease to the accumulated strain value greater than the significance threshold.

Furthermore, as shown in FIG. 6C, the visualization of the accumulated strain 621 for the user of the electronic device 120 includes a current accumulated strain value indicator 632A for the time indicator 634A, and the visualization of the accumulated strain 621 is associated with a first appearance (e.g., white) based on the magnitude of the current accumulated strain value indicator 632A. In some implementations, the appearance of the visualization of the accumulated strain 621 changes based on the current magnitude accumulated of the strain value indicator for the current time indicator.

In some implementations, the significance threshold is deterministic or non-deterministic based on the number of identified instances in which the head pose information changes (and/or the body pose information changes) associated with the user caused an increase or a decrease to the accumulated strain value greater than the significance threshold. For example, the significance threshold changes such that only N instances are shown by the animation. In some implementations, the significance threshold is deterministic or non-deterministic based on user preferences, user history, or the like. For example, the significance threshold may be higher for a user associated with frequent large variances in the accumulated strain value, whereas the significance threshold may be lower for a user associated with smaller variances in the accumulated strain value. As such, the one or more instances are selected as "highlights" to be viewed by the user. However, the user may scrub to any time on the timeline by, for example, dragging the current time indicator or providing a time via a voice command.

As shown in FIG. 6C, in response to detecting the second user input 622 directed to the first affordance 612 in FIG. 6B, the electronic device 120 also presents a third affordance 631 for initiating a stretching session. In some implementations, an appearance of the second affordance 619 and the third affordance 631 change to represent the accumulated strain value for the user over the respective time window. For example, the appearance of the second affordance 619 and the third affordance 631 correspond to the first appearance (e.g., white) associated with the visualization of the accumulated strain 621. As such, the appearance of the second affordance 619 and the third affordance 631 also change based on the current magnitude accumulated of the strain value indicator for the current time indicator.

Figure 6D:
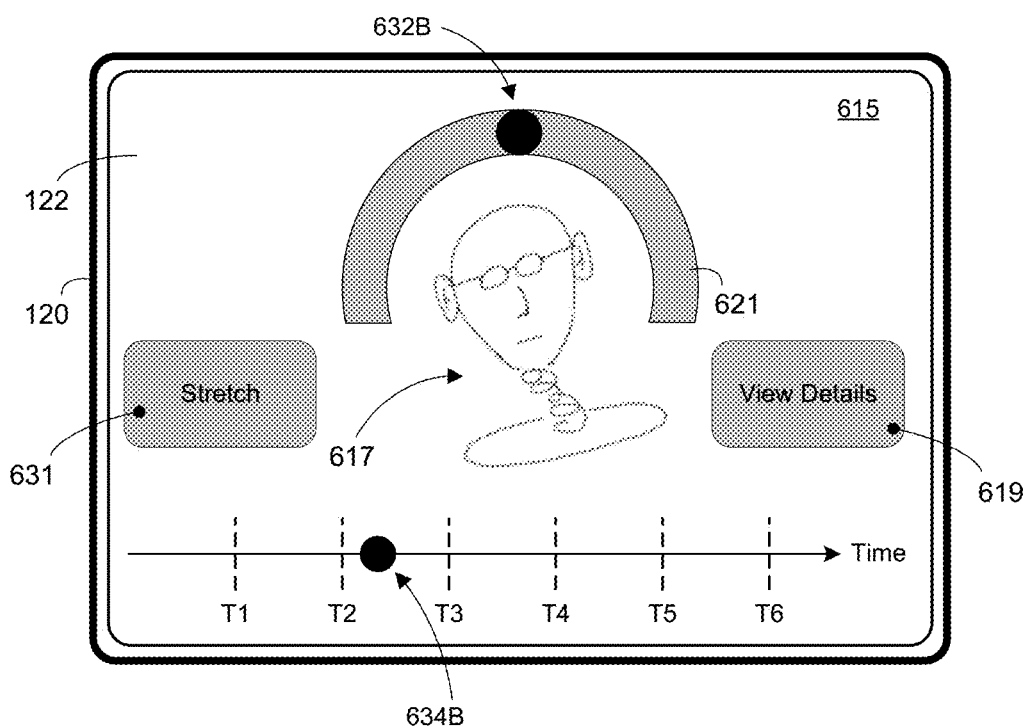

As shown in FIG. 6D, the electronic device 120 continues presentation of the animation of the representation of the user 617 over the respective time window that corresponds to one or more instances in which the head pose information changes (and/or the body pose information changes) associated with the user caused an increase or a decrease to the accumulated strain value greater than the significance threshold. As shown in FIG. 6D, the electronic device 120 presents the timeline with a time indicator 634B that corresponds to a second instance among the one or more instances in which the head pose information changes (and/or the body pose information changes) associated with the user caused an increase or a decrease to the accumulated strain value greater than the significance threshold.

Furthermore, as shown in FIG. 6D, the visualization of the accumulated strain 621 for the user of the electronic device 120 includes a current accumulated strain value indicator 632B for the time indicator 634B, and the visualization of the accumulated strain 621 is associated with a second appearance (e.g., light grey) based on the magnitude of the current accumulated strain value indicator 632B that is greater than the magnitude of the accumulated strain value indicator 632A in FIG. 6C. According to some implementations, the representation of the user 617 is animated according to the head pose information changes (and/or the body pose information changes) during the one or more instances within the respective time window (e.g., the second instance in FIG. 6D).

Figure 6E:
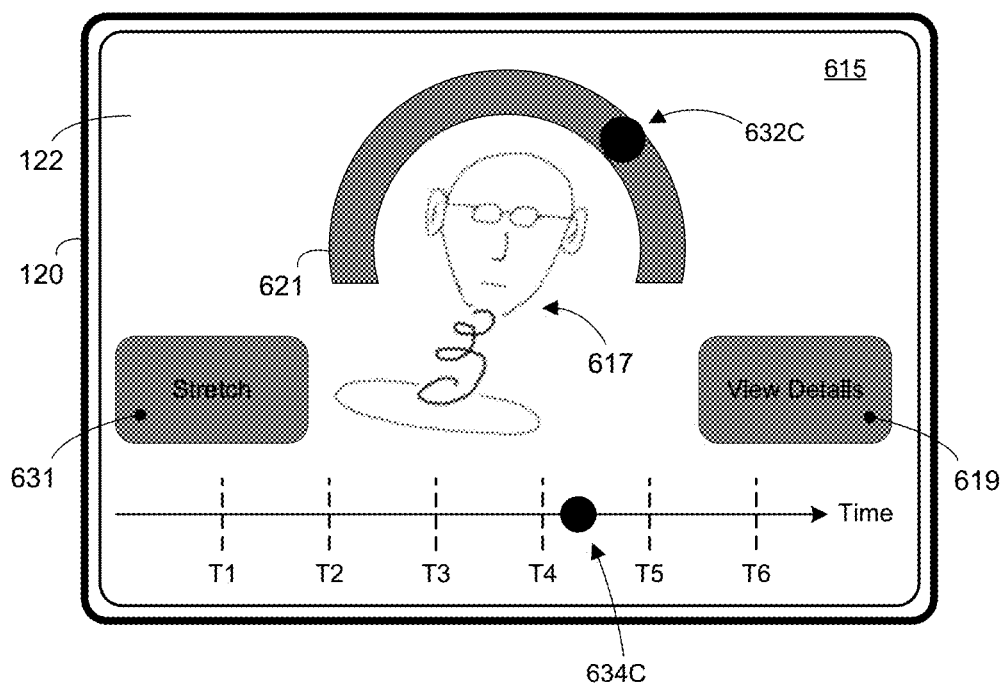

As shown in FIG. 6E, the electronic device 120 continues presentation of the animation of the representation of the user 617 over the respective time window that corresponds to one or more instances in which the head pose information changes (and/or the body pose information changes) associated with the user caused an increase or a decrease to the accumulated strain value greater than the significance threshold. As shown in FIG. 6E, the electronic device 120 presents the timeline with a time indicator 634C that corresponds to a third instance among the one or more instances in which the head pose information changes (and/or the body pose information changes) associated with the user caused an increase or a decrease to the accumulated strain value greater than the significance threshold.

Furthermore, as shown in FIG. 6E, the visualization of the accumulated strain 621 for the user of the electronic device 120 includes a current accumulated strain value indicator 632C for the time indicator 634C, and the visualization of the accumulated strain 621 is associated with a third appearance (e.g., dark grey) based on the magnitude of the current accumulated strain value indicator 632C that is greater than the magnitude of the accumulated strain value indicator 632B in FIG. 6D. According to some implementations, the representation of the user 617 is animated according to the head pose information changes (and/or the body pose information changes) during the one or more instances within the respective time window (e.g., the third instance in FIG. 6E).

Figure 6F:
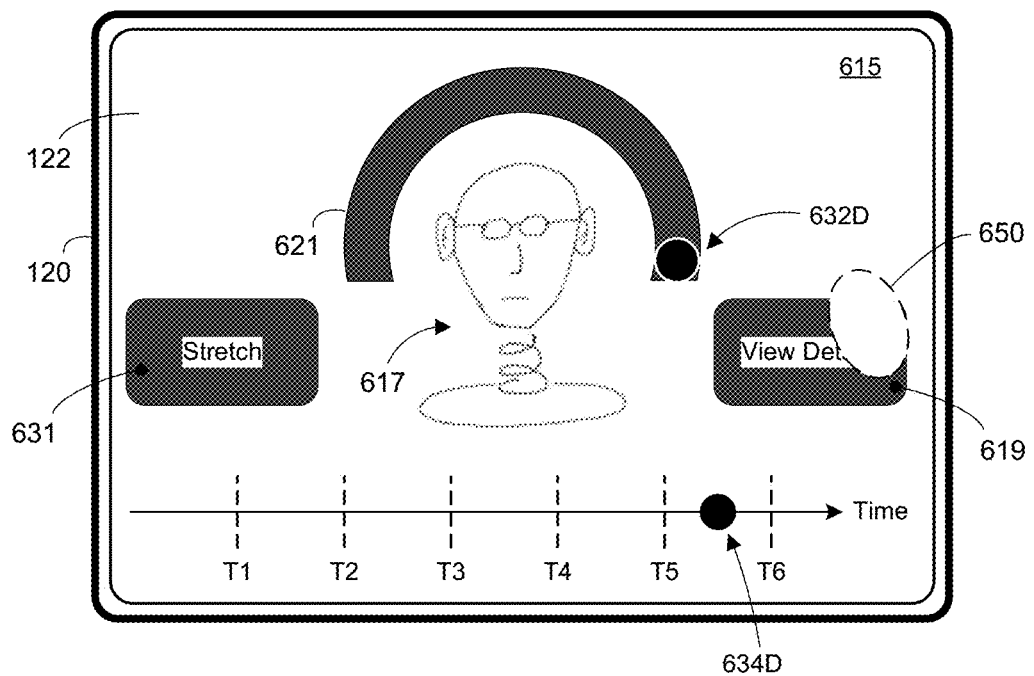

As shown in FIG. 6F, the electronic device 120 continues presentation of the animation of the representation of the user 617 over the respective time window that corresponds to one or more instances in which the head pose information changes (and/or the body pose information changes) associated with the user caused an increase or a decrease to the accumulated strain value greater than the significance threshold. As shown in FIG. 6F, the electronic device 120 presents the timeline with a time indicator 634D that corresponds to a fourth instance among the one or more instances in which the head pose information changes (and/or the body pose information changes) associated with the user caused an increase or a decrease to the accumulated strain value greater than the significance threshold.

Furthermore, as shown in FIG. 6F, the visualization of the accumulated strain 621 for the user of the electronic device 120 includes a current accumulated strain value indicator 632D for the time indicator 634D, and the visualization of the accumulated strain 621 is associated with a fourth appearance (e.g., black) based on the magnitude of the current accumulated strain value indicator 632D that is greater than the magnitude of the accumulated strain value indicator 632C in FIG. 6E. According to some implementations, the representation of the user 617 is animated according to the head pose information changes (and/or the body pose information changes) during the one or more instances within the respective time window (e.g., the fourth instance in FIG. 6F).

Figure 6G:
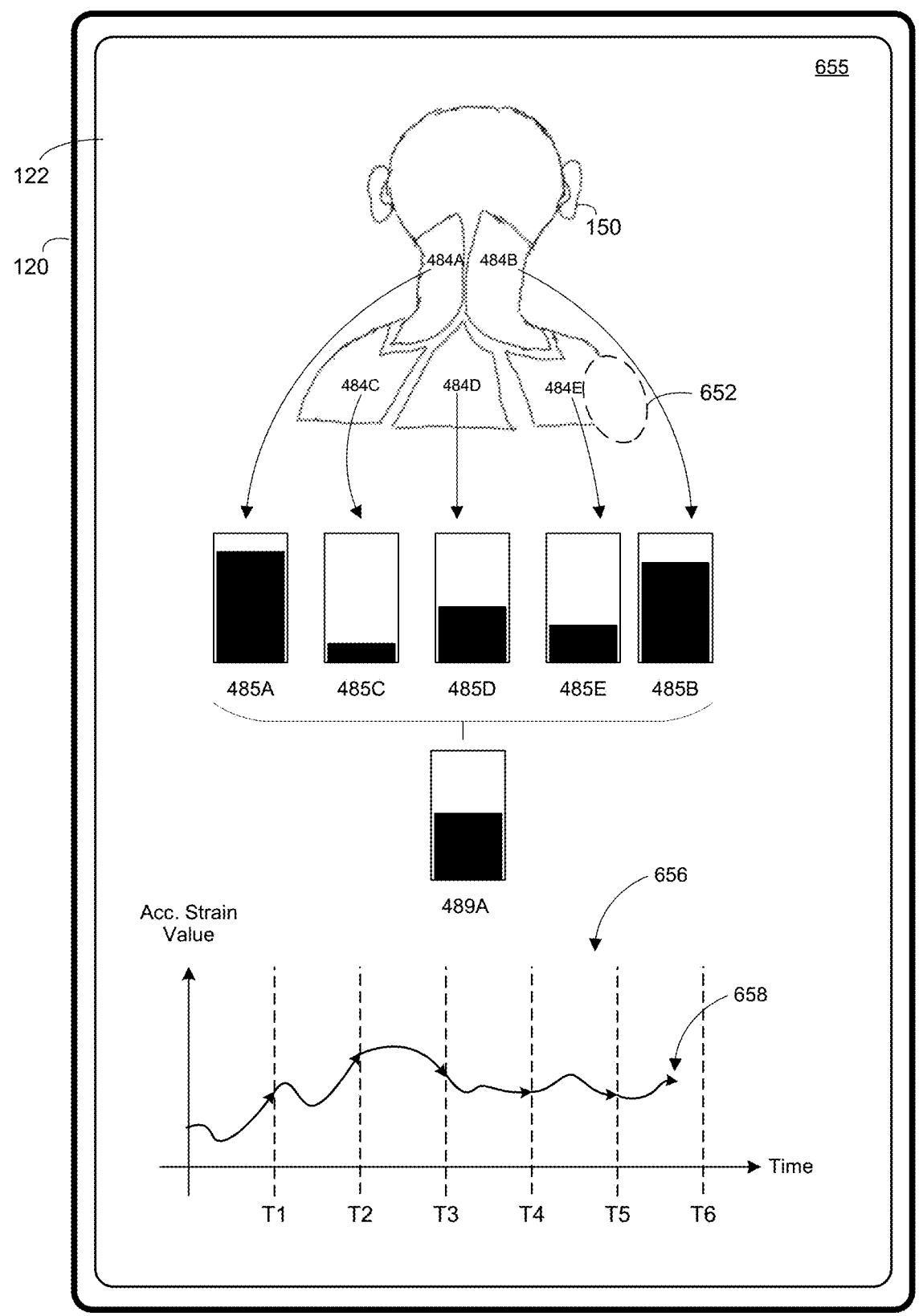

As shown in FIG. 6F, the electronic device 120 detects a third user input 650 (e.g., tap input, touch input, or the like) directed to the second affordance 619 (e.g., via the display 122—a touchscreen). As shown in FIG. 6G, in response to detecting the third user input 650 directed to the second affordance 619 in FIG. 6F, the electronic device 120 presents a detailed accumulated strain interface 655.

As shown in FIG. 6G, the detailed accumulated strain interface 655 includes a graph 656 of the accumulated strain value over at least the respective time window, where the endpoint 658 corresponds to the magnitude of the current accumulated strain value indicator 624A in FIG. 6B. Furthermore, as shown in FIG. 6G, the detailed accumulated strain interface 655 also includes an illustration of the muscles or muscle groups/regions 484A, 484B, 484C, 484D, and 484E of the user 150 as well as current accumulated muscle strain values 485A, 485B, 485C, 485D, and 485E for the muscles or muscle groups/regions 484A, 484B, 484C, 484D, and 484E, respectively. One of ordinary skill in the art will appreciate that the detailed accumulated strain interface 655 may be formatted or structured in myriad ways in various other implementations.

Figure 6H:
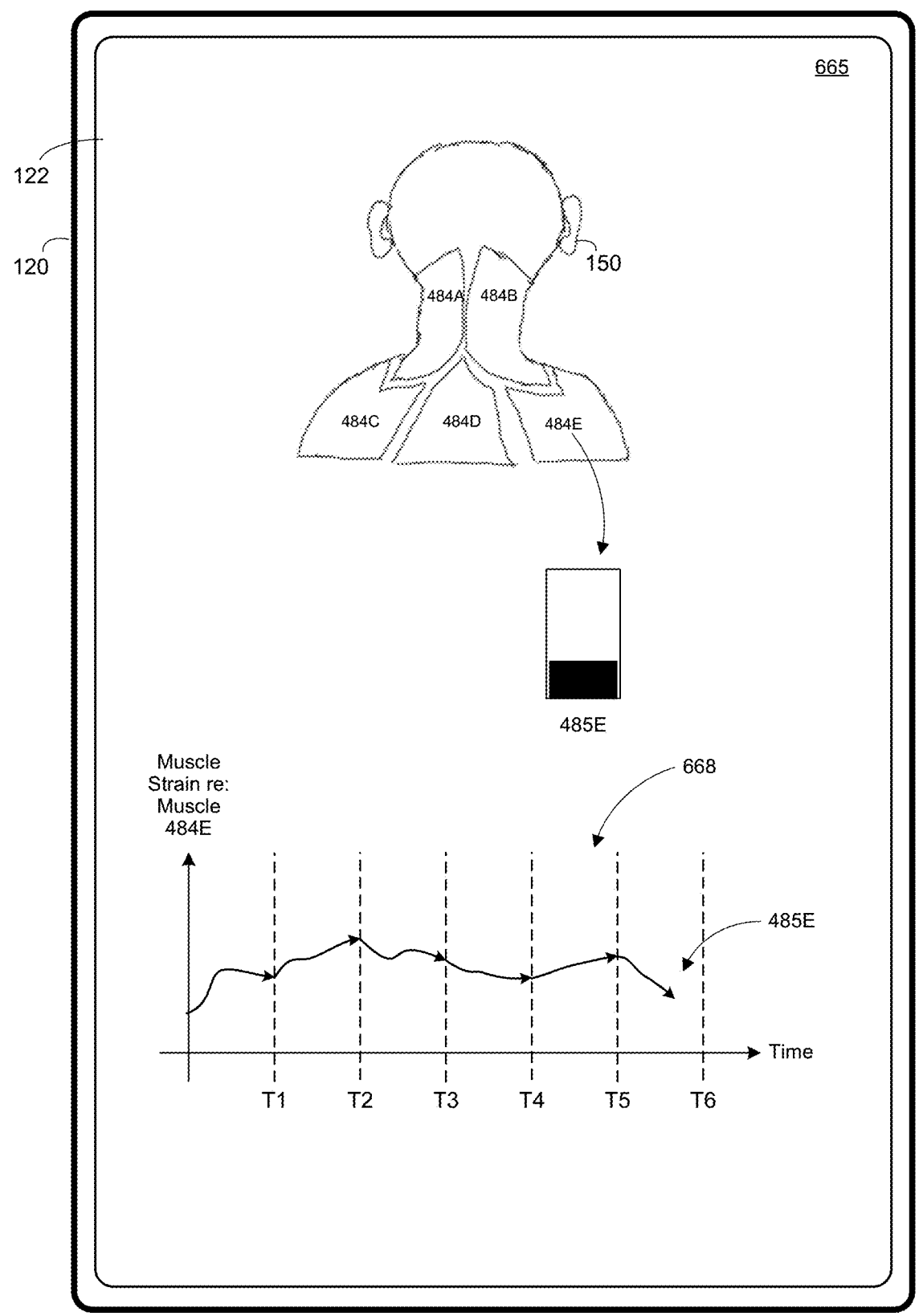

As shown in FIG. 6G, the electronic device 120 detects a fourth user input 652 (e.g., tap input, touch input, or the like) directed to the muscle or muscle group/region 484E (e.g., via the display 122—a touchscreen). As shown in FIG. 6H, in response to detecting the fourth user input 652 directed to the muscle or muscle group/region 484E in FIG. 6G, the electronic device 120 presents a detailed muscle strain interface 665 for the muscle or muscle group/region 484E. As shown in FIG. 6H, the detailed muscle strain interface 665 includes a graph 668 of the muscle strain value 485E over at least the respective time window, where the endpoint corresponds to the current muscle strain value 485E. As such, the user may drill down into muscle or muscle group/region specific information from the detailed accumulated strain interface 655 in FIG. 6G. One of ordinary skill in the art will appreciate that the detailed muscle strain interface 665 may be formatted or structured in myriad ways in various other implementations.

Figure 7A:
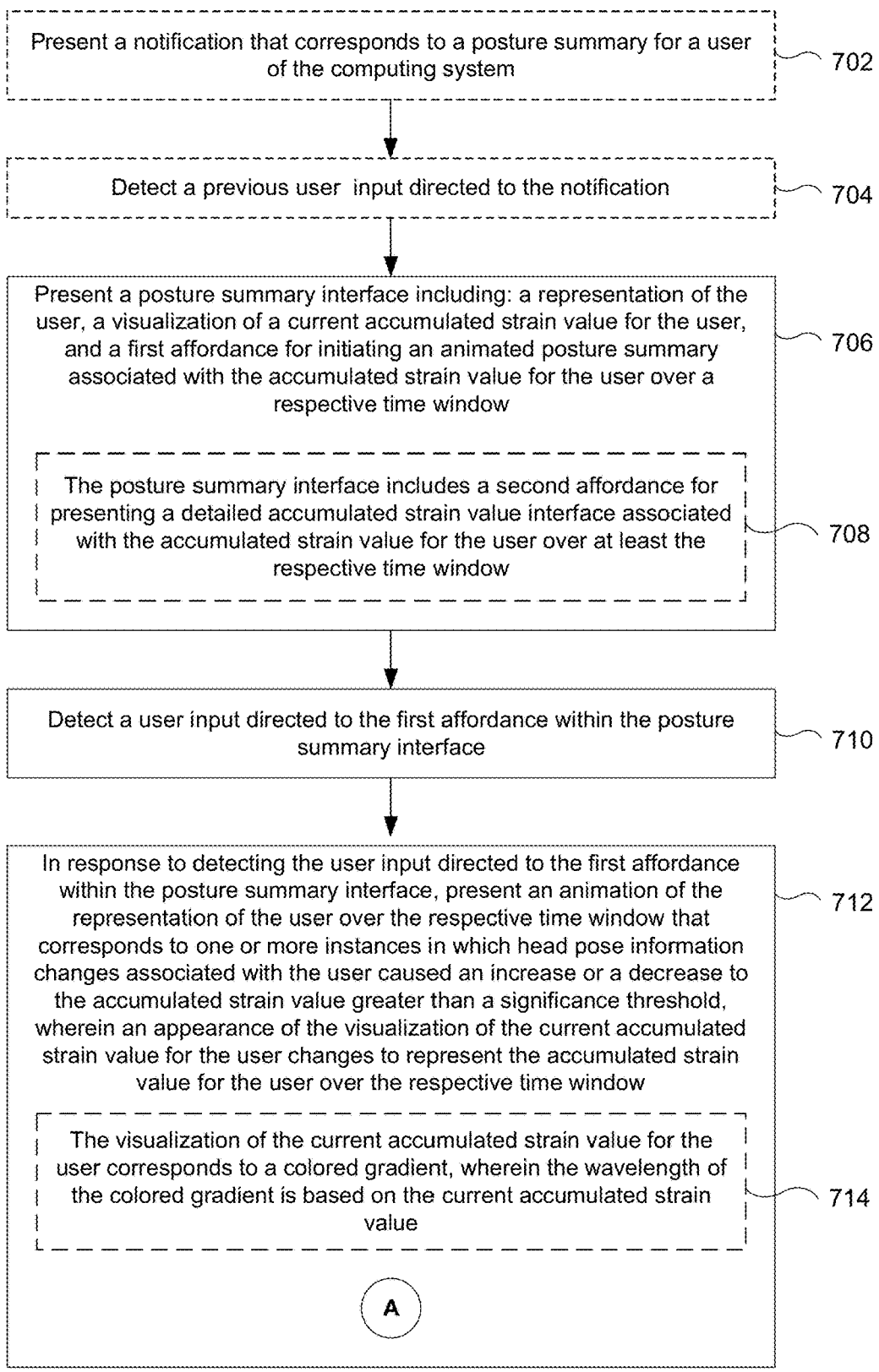
FIGS. 7A and 7B illustrate a flowchart representation of a method of surfacing accumulated strain information in accordance with some implementations.
Figure 7B:
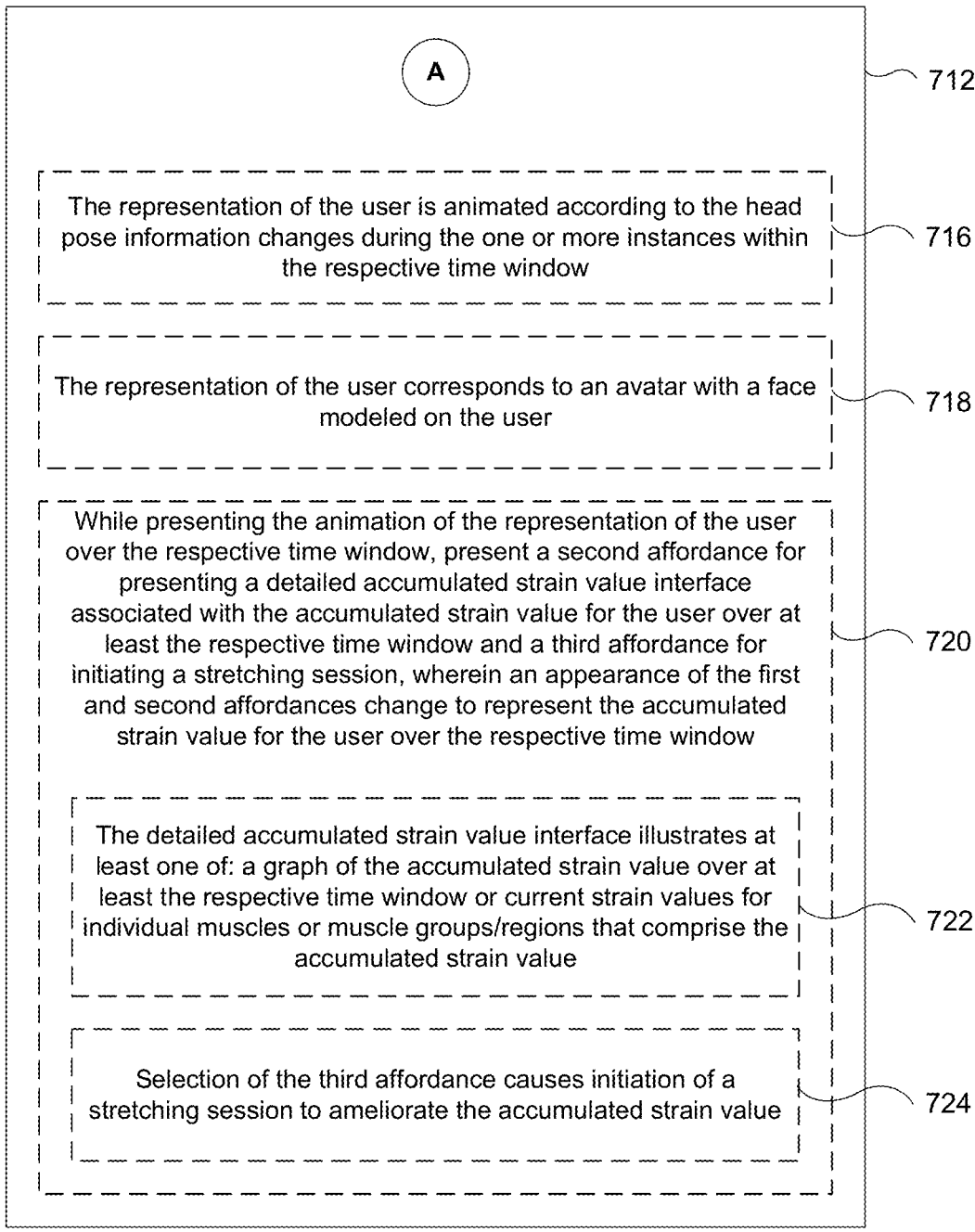

FIGS. 7A and 7B illustrate a flowchart representation of a method 700 of surfacing accumulated strain information with some implementations. In various implementations, the method 700 is performed at a computing system including non-transitory memory and one or more processors, wherein the computing system is communicatively coupled to a display device and one or more input devices (e.g., the electronic device 120 shown in FIGS. 1 and 3; the controller 110 in FIGS. 1 and 2; or a suitable combination thereof). In some implementations, the method 700 is performed by processing logic, including hardware, firmware, software, or a combination thereof. In some implementations, the method 700 is performed by a processor executing code stored in a non-transitory computer-readable medium (e.g., a memory). In some implementations, the computing system corresponds to one of a tablet, a laptop, a mobile phone, a near-eye system, a wearable computing device, or the like. In some implementations, the one or more input devices correspond to a computer vision (CV) engine that uses an image stream from one or more exterior-facing image sensors, a finger/hand/extremity tracking engine, an eye tracking engine, a touch-sensitive surface, one or more microphones, and/or the like.

As discussed above, many persons (e.g., the user 150 in FIG. 1) may spend a significant number of hours at their computers or other devices during both work and non-work hours. This time spent using a computer or other devices may negatively impact the posture of said person. As such, described herein is a method and device for promoting posture awareness by surfacing accumulated strain information.

According to some implementations, as represented by block 702, the method 700 includes presenting, via the display device, a notification that corresponds to a posture summary for a user of the computing system. In some implementations, the computing system overlays the notification on current content such as a two-dimensional (2D) graphical user interface (GUI) or a three-dimensional (3D) environment. In some implementations, the computing system composites the notification with the current content such as the 3D environment. In some implementations, the notification corresponds to 2D content or volumetric/3D virtual content. In some implementations, the notification acts as an affordance that may be selected with a touch input, hand tracking input, gaze input, voice command, or the like.

As one example, with reference to FIG. 6A, the electronic device 120 presents a notification 602 overlaid on a home interface 605, wherein the notification 602 corresponds to a posture summary for a user of the electronic device 120 based on accumulated muscle strain. For example, with reference to FIG. 5, the computing system or a portion thereof (e.g., the rendering engine 550) renders one or more images frames for a GUI or an XR environment (e.g., a 3D environment), and the computing system or a portion thereof (e.g., the presenter 560) presents the rendered image frames for the GUI or the XR environment to the user 150 via the one or more displays 312. In some implementations, the display device corresponds to a transparent lens assembly, and wherein presenting the XR environment includes projecting at least a portion of the XR environment onto the transparent lens assembly. In some implementations, the display device corresponds to a near-eye system, and wherein presenting the XR environment includes compositing at least a portion of the XR environment with one or more images of a physical environment captured by an exterior-facing image sensor.

According to some implementations, the computing system surfaces the notification when the respective time window, which is mentioned below with respect to block 706, elapses. In some implementations, the computing system surfaces the notification once a day, twice a day, at a user-specified time, when the accumulated strain value reaches a deterministic or non-deterministic value, or the like.

According to some implementations, as represented by block 704, the method 700 includes detecting a previous user input, via the one or more input devices, directed to the notification. In some implementations, the first user input corresponds to one of a touch input directed to the display device, a voice input, a gaze input, or a hand/extremity tracking input. As one example, with reference to FIG. 6A, the electronic device 120 detects a first user input 604 (e.g., tap input, touch input, or the like) directed to the notification 602 (e.g., via the display 122—a touchscreen).

As represented by block 706, the method 700 includes presenting, via the display device, a posture summary interface including: a representation of the user, a visualization of a current accumulated strain value for the user, and a first affordance for initiating an animated posture summary associated with the accumulated strain value for the user over a respective time window. In some implementations, the respective time window corresponds to a deterministic or non-deterministic length of time such as the last week, the last X days, the last day, the last Y hours, the last hour, the last Z minutes, workday, workout session, or the like. According to some implementations, the computing system presents the posture summary interface in response to detecting the previous input directed to the notification as described in block 704. According to some implementations, the computing system presents the posture summary interface when the respective time window elapses. According to some implementations, the computing system presents the posture summary interface once a day, twice a day, at a user-specified time, when the accumulated strain value reaches a deterministic or non-deterministic value, or the like.

As one example, with reference to FIG. 6B, in response to detecting the first user input 604 directed to the notification 602 in FIG. 6A, the electronic device 120 presents a posture summary interface 615 on the display. Continuing with this example, the posture summary interface 615 in FIG. 6B includes a representation of the user 617 such as an avatar modeled on the face and/or body of the user of the electronic device 120. Continuing with this example, the posture summary interface 615 in FIG. 6B also includes a visualization of the accumulated strain 621 for the user of the electronic device 120 with a current accumulated strain value indicator 624A. According to some implementations, the accumulated (muscle) strain is based on the strain information 480, which includes a current accumulated strain value 489A (e.g., associated with the current accumulated strain value indicator 624A) corresponding to a function of one or more of the current muscle strain values 485A, 485B, 485C, 485D, and 485E for muscles or muscle groups/regions 484A, 484B, 484C, 484D, and 484E, respectively, of the user 150 (e.g., as shown in FIG. 4D). Continuing with this example, the posture summary interface 615 in FIG. 6B further includes a first affordance 612 for initiating an animated posture summary associated with the accumulated strain for the user over a respective time window. For example, the first affordance 612 may be selected with a touch input, hand tracking input, gaze input, voice command, or the like.

In some implementations, as represented by block 708, the posture summary interface includes a second affordance for presenting a detailed accumulated strain value interface associated with the accumulated strain value for the user over at least the respective time window. As one example, the posture summary interface 615 in FIG. 6B includes a second affordance 619 for presenting a detailed accumulated strain interface associated with the accumulated strain value for the user over at least the respective time window (e.g., shown in FIG. 6H). For example, the second affordance 619 may be selected with a touch input, hand tracking input, gaze input, voice command, or the like.

As represented by block 710, the method 700 includes detecting a user input, via the one or more input devices, directed to the first affordance within the posture summary interface. In some implementations, the second user input corresponds to one of a touch input directed to the display device, a voice input, a gaze input, or a hand/extremity tracking input. As one example, with reference to FIG. 6B, the electronic device 120 detects a second user input 622 (e.g., tap input, touch input, or the like) directed to the first affordance 612 (e.g., via the display 122—a touchscreen).

As represented by block 712, in response to detecting the user input directed to the first affordance within the posture summary interface, the method 700 includes presenting, via the display device, an animation of the representation of the user over the respective time window that corresponds to one or more instances in which head pose information changes (and/or body pose information changes) associated with the user caused an increase or a decrease to the accumulated strain value greater than a significance threshold, wherein an appearance of the visualization of the current accumulated strain value for the user changes to represent the accumulated strain value for the user over the respective time window. In some implementations, the head pose information changes correspond to displacement, velocity, acceleration, jerk, etc. of the head pose information. When body pose information is considered, the body pose information changes correspond to displacement, velocity, acceleration, jerk, etc. of the body pose information. In some implementations, the computing systems removes the first affordance from the posture summary interface in response to detecting the user input directed to the first affordance. In some implementations, the visual animation of the one or more instances (e.g., as shown in FIGS. 6C-6F) in which the head pose information changes (and/or the body pose information changes) associated with the user caused an increase or a decrease to the accumulated strain value greater than the significance threshold may be correlated with audio feedback, haptic feedback, additional visual feedback (e.g., increased or decreased brightness, contrast, etc.), and/or the like to further indicate the increases or decreases to the accumulated strain value.

In some implementations, the significance threshold is deterministic or non-deterministic based on the number of identified instances. For example, the significance threshold changes such that only N instances are shown by the animation. In some implementations, the significance threshold is deterministic or non-deterministic based on use preferences, user history, or the like. For example, the significance threshold may be higher for a user associated with frequent large variances in the accumulated strain value, whereas the significance threshold may be lower for a user associated with smaller variances in the accumulated strain value. As such, the one or more instances are selected as "highlights" to be viewed by the user. However, the user is able to scrub to any timestamp within the respective time window.

As one example, with reference to the sequence in FIGS. 6C-6F, in response to detecting the second user input 622 directed to the first affordance 612 in FIG. 6B, the electronic device 120 presents an animation of the representation of the user 617 over the respective time window that corresponds to one or more instances in which head pose information changes (and/or body pose information changes) associated with the user caused an increase or a decrease to the accumulated strain value greater than a significance threshold. According to some implementations, the representation of the user 617 is animated according to the head pose information changes (and/or the body pose information changes) during the one or more instances within the respective time window (e.g., the first through fourth instances in FIGS. 6C-6F). Continuing with this example, FIG. 6C shows a first instance associated with the time indicator 634A among the one or more instances in which the head pose information changes (and/or the body pose information changes) associated with the user caused an increase or a decrease to the accumulated strain value greater than the significance threshold.

Continuing with the above example, FIG. 6D shows a second instance associated with the time indicator 634B among the one or more instances in which the head pose information changes (and/or the body pose information changes) associated with the user caused an increase or a decrease to the accumulated strain value greater than the significance threshold. Continuing with this example, FIG. 6E shows a third instance associated with the time indicator 634C among the one or more instances in which the head pose information changes (and/or the body pose information changes) associated with the user caused an increase or a decrease to the accumulated strain value greater than the significance threshold. Continuing with this example, FIG. 6F shows a fourth instance associated with the time indicator 634D among the one or more instances in which the head pose information changes (and/or the body pose information changes) associated with the user caused an increase or a decrease to the accumulated strain value greater than the significance threshold. As such, the one or more instances are selected as "highlights" to be viewed by the user. However, the user may scrub to any time on the timeline by, for example, dragging the current time indicator or providing a time via a voice command.

In some implementations, the head pose information at least includes three degrees of freedom (3DOF) rotational values. For example, with reference to FIGS. 4A and 4B, the computing system or a portion thereof (e.g., the head/body pose tracking engine 414) obtains (e.g., receives, retrieves, or detects/determines/generates) a pose characterization vector 415 based on the input data and updates the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like.

In some implementations, the body pose information at least includes 3DOF rotational values. For example, with reference to FIGS. 4A and 4B, the computing system or a portion thereof (e.g., the head/body pose tracking engine 414) obtains (e.g., receives, retrieves, or detects/determines/generates) a pose characterization vector 415 based on the input data and updates the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like.

For example, with reference to FIG. 4C, the computing system or a portion thereof (e.g., the head/body/neck mechanics engine 462) obtains (e.g., receives, retrieves, or determines/generates) displacement, velocity, acceleration, jerk, torque, etc. values for the head/body/neck of the user 150 based on changes to the pose characterization vector 415. With continued reference to FIG. 4C, the computing system or a portion thereof (e.g., the strain analyzer 464) determines current strain information 480 for one or more muscles or muscle groups based on: the displacement, velocity, acceleration, jerk, torque, etc. values for the head/body/neck of the user 150 from the head/body/neck mechanics engine 462; historical information 466; and the context information vector 470. In some implementations, the strain analyzer 464 determines the current strain information 480 based on strain increase logic 465A and/or strain decrease logic 465B. As shown in FIG. 4D, the current strain information 480 includes accumulated strain information 486: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information.

In some implementations, as represented by block 714, the visualization of the current accumulated strain value for the user corresponds to a colored gradient, wherein the wavelength of the colored gradient is based on the current accumulated strain value. In some implementations, the wavelength of the colored gradient changes from green to red as the accumulated neck strain increases. In some implementations, the opposite occurs as the accumulated neck strain decreases.

As one example, with reference to the sequence in FIGS. 6C-6F, the appearance of the visualization of the accumulated strain 621 changes based on the current magnitude accumulated of the strain value indicator for the current time indicator. As one example, with reference to FIG. 6C, the visualization of the accumulated strain 621 is associated with a first appearance (e.g., white) based on the magnitude of the current accumulated strain value indicator 632A. As another example, with reference to FIG. 6D, the visualization of the accumulated strain 621 is associated with a second appearance (e.g., light grey) based on the magnitude of the current accumulated strain value indicator 632B that is greater than the magnitude of the accumulated strain value indicator 632A in FIG. 6C.

As yet another example, with reference to FIG. 6E, the visualization of the accumulated strain 621 is associated with a third appearance (e.g., dark grey) based on the magnitude of the current accumulated strain value indicator 632C that is greater than the magnitude of the accumulated strain value indicator 632B in FIG. 6D. As yet another example, with reference to FIG. 6F, the visualization of the accumulated strain 621 is associated with a fourth appearance (e.g., black) based on the magnitude of the current accumulated strain value indicator 632D that is greater than the magnitude of the accumulated strain value indicator 632C in FIG. 6E. As such, with reference to FIGS. 6C-6F, the appearance of the visualization of the accumulated strain 621 darkens as the accumulated strain value increases, and the appearance of the visualization of the accumulated strain 621 would lighten if the accumulated strain value decreased.

In some implementations, as represented by block 716, the representation of the user is animated according to the head pose information changes (and/or the body pose information changes) during the one or more instances within the respective time window. As mentioned above, in some implementations, the representation of the user 617 is animated according to the head pose information changes (and/or the body pose information changes) during the one or more instances within the respective time window (e.g., the first through fourth instances in FIGS. 6C-6F, respectively). In some implementations, as represented by block 718, the representation of the user corresponds to an avatar with a face (and/or a body) modeled on the user of the computing system.

In some implementations, as represented by block 720, while presenting the animation of the representation of the user over the respective time window, the method 700 includes presenting, via the display device, a second affordance for presenting a detailed accumulated strain value interface associated with the accumulated strain value for the user over at least the respective time window and a third affordance for initiating a stretching session, wherein an appearance of the first and second affordances change to represent the accumulated strain value for the user over the respective time window. As one example, in FIGS. 6C-6F, the posture summary interface 615 includes a second affordance 619 for presenting a detailed accumulated strain interface associated with the accumulated strain value for the user over at least the respective time window (e.g., shown in FIG. 6H) and a third affordance 631 for initiating a stretching session.

In some implementations, an appearance of the second affordance 619 and the third affordance 631 within the posture summary interface 615 change to represent the accumulated strain value for the user over the respective time window. For example, with reference to FIG. 6C, the appearance of the second affordance 619 and the third affordance 631 correspond to the first appearance (e.g., white) associated with the visualization of the accumulated strain 621. As such, the appearance of the second affordance 619 and the third affordance 631 also change based on the current magnitude accumulated of the strain value indicator for the current time indicator.

In some implementations, as represented by block 722, the detailed accumulated strain value interface illustrates at least one of: a graph of the accumulated strain value over at least the respective time window or current strain values for individual muscles or muscle groups/regions that comprise the accumulated strain value. In some implementations, the detailed accumulated strain value interface illustrates a graph of the accumulated strain value over at least the respective time window. For example, the graph may include previous time windows as well to provide additional context. In some implementations, the detailed accumulated strain value interface also illustrates a current accumulated strain value and (optionally) current strain values for individual muscles or muscle groups/regions. In some implementations, the user may select a specific muscle or muscle group/region to drill down in order to show details information for the specific muscle or muscle group/region.

As one example, with reference to FIG. 6F, the electronic device 120 detects a third user input 650 (e.g., tap input, touch input, or the like) directed to the second affordance 619 (e.g., via the display 122—a touchscreen). Continuing with the example, in response to detecting the third user input 650 directed to the second affordance 619 in FIG. 6F, the electronic device 120 presents a detailed accumulated strain interface 655 in FIG. 6G.

As shown in FIG. 6G, for example, the detailed accumulated strain interface 655 includes a graph 656 of the accumulated strain value over at least the respective time window, where the endpoint 658 corresponds to the magnitude of the current accumulated strain value indicator 624A in FIG. 6B. Furthermore, as shown in FIG. 6G, the detailed accumulated strain interface 655 also includes an illustration of the muscles or muscle groups/regions 484A, 484B, 484C, 484D, and 484E of the user 150 as well as current accumulated muscle strain values 485A, 485B, 485C, 485D, and 485E for the muscles or muscle groups/regions 484A, 484B, 484C, 484D, and 484E, respectively. In some implementations, the user may drill down into detailed muscle strain information for a specific muscle or muscle group/region as illustrated by the detailed muscle strain interface 665 in FIG. 6H.

In some implementations, the accumulated strain value is based on a plurality of strain values for a plurality of muscles or muscle groups/regions of the user. In some implementations, the accumulated strain value is a function of the plurality of strain values for the plurality of muscles or muscle groups/regions of the user. For example, some muscles or muscle groups/regions may be weighted differently based on user preferences, user history, or the like. As shown in FIG. 4D, the current strain information 480 includes accumulated strain information 486 with: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information.

In some implementations, as represented by block 724, selection of the third affordance causes initiation of a stretching session to ameliorate the accumulated strain value. In some implementations, the third affordance initiates a stretching session. For example, the computing system may present the stretching session based on U.S. Non-Provisional patent application Ser. No. 18/200,542, filed on May 22, 2023, which is incorporated by reference in its entirety.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first media item could be termed a second media item, and, similarly, a second media item could be termed a first media item, which changing the meaning of the description, so long as the occurrences of the "first media item" are renamed consistently and the occurrences of the "second media item" are renamed consistently. The first media item and the second media item are both media items, but they are not the same media item.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
   at a computing system including non-transitory memory and one or more processors, wherein the computing system is communicatively coupled to a display device and one or more input devices via a communication interface:
   determining a plurality of muscle strain values for a respective plurality of muscle regions based on head pose information of a user over a time window;
   detecting, via the one or more input devices, a user input to display a muscle strain interface; and
   in response to detecting the user input, displaying the muscle strain interface including:
   a representation of the user including the plurality of muscle regions; and
   a plurality of visualizations of the plurality of muscle strain values respectively displayed in association with the plurality of muscle regions.

2. The method of claim 1, further comprising:
   determining an accumulated muscle strain value based on the plurality of muscle strain values, wherein the muscle strain interface further includes a visualization of the accumulated muscle strain value.

3. The method of claim 2, wherein the muscle strain interface further includes a graph of the accumulated muscle strain value over the time window.

4. The method of claim 1, further comprising:
   detecting, via the one or more input devices, a user input selecting a particular muscle region of the plurality of muscle regions; and in response to detecting the user input selecting the particular muscle region, displaying a graph of a muscle strain value for the particular muscle region over the time window.

5. The method of claim 1, wherein determining the plurality of muscle strain values includes determining displacement, velocity, or acceleration values for a head of the user.

6. The method of claim 1, wherein a particular visualization of the plurality of visualizations for a particular muscle strain value of the plurality of muscle strain values has a color based on the particular muscle strain value.

7. The method of claim 1, wherein a particular visualization of the plurality of visualizations for a particular muscle strain value of the plurality of muscle strain values has a size based on the particular muscle strain value.

8. The method of claim 1, wherein the user input corresponds to one of a touch input directed to the display device, a voice input, a gaze input, or a hand/extremity tracking input.

9. The method of claim 1, wherein the user input corresponds to a user input directed to an affordance.

10. A device comprising:
one or more processors;
a non-transitory memory;
an interface for communicating with a display device and one or more input devices; and
one or more programs stored in the non-transitory memory, which, when executed by the one or more processors, cause the device to:
determine a plurality of muscle strain values for a respective plurality of muscle regions based on head pose information of a user over a time window;
detect, via the one or more input devices, a user input to display a muscle strain interface; and
in response to detecting the user input, display the muscle strain interface including:
a representation of the user including the plurality of muscle regions; and
a plurality of visualizations of the plurality of muscle strain values respectively displayed in association with the plurality of muscle regions.

11. The device of claim 10, wherein the one or more programs further cause the device to:
determine an accumulated muscle strain value based on the plurality of muscle strain values, wherein the muscle strain interface further includes a visualization of the accumulated muscle strain value.

12. The device of claim 11, wherein the muscle strain interface further includes a graph of the accumulated muscle strain value over the time window.

13. The device of claim 10, wherein the one or more programs further cause the device to:
detect, via the one or more input devices, a user input selecting a particular muscle region of the plurality of muscle regions; and
in response to detecting the user input selecting the particular muscle region, display a graph of a muscle strain value for the particular muscle region over the time window.

14. The device of claim 10, wherein a particular visualization of the plurality of visualizations for a particular muscle strain value of the plurality of muscle strain values has a color based on the particular muscle strain value.

15. The device of claim 10, wherein a particular visualization of the plurality of visualizations for a particular muscle strain value of the plurality of muscle strain values has a size based on the particular muscle strain value.

16. The device of claim 10, wherein the user input corresponds to a user input directed to an affordance.

17. A non-transitory memory storing one or more programs, which, when executed by one or more processors of a device with an interface for communicating with a display device and one or more input devices, cause the device to:
determine a plurality of muscle strain values for a respective plurality of muscle regions based on head pose information of a user over a time window;
detect, via the one or more input devices, a user input to display a muscle strain interface; and
in response to detecting the user input, display the muscle strain interface including:
a representation of the user including the plurality of muscle regions; and
a plurality of visualizations of the plurality of muscle strain values respectively displayed in association with the plurality of muscle regions.

18. The non-transitory memory of claim 17, wherein the one or more programs further cause the device to:
determine an accumulated muscle strain value based on the plurality of muscle strain values, wherein the muscle strain interface further includes a visualization of the accumulated muscle strain value.

19. The non-transitory memory of claim 18, wherein the muscle strain interface further includes a graph of the accumulated muscle strain value over the time window.

20. The non-transitory memory of claim 17, wherein the one or more programs further cause the device to:
detect, via the one or more input devices, a user input selecting a particular muscle region of the plurality of muscle regions; and
in response to detecting the user input selecting the particular muscle region, display a graph of a muscle strain value for the particular muscle region over the time window.

* * * * *